United States Patent [19]

Kun et al.

[11] Patent Number: 5,482,975
[45] Date of Patent: Jan. 9, 1996

[54] ADENOSINE DIPHOSPHORIBOSE POLYMERASE BINDING NITROSO AROMATIC COMPOUNDS USEFUL AS RETROVIRAL INACTIVATING AGENTS, ANTI-RETROVIRAL AGENTS AND ANTI-TUMOR AGENTS

[75] Inventors: Ernest Kun, Mill Valley; Jerome Mendeleyev, San Francisco, both of Calif.

[73] Assignee: Octamer, Inc., Mill Valley, Calif.

[21] Appl. No.: 21,830

[22] Filed: Feb. 24, 1993

Related U.S. Application Data

[63] Continuation-in-part of Ser. No. 893,429, Jun. 4, 1992, abandoned, which is a continuation-in-part of Ser. No. 780,809, Oct. 22, 1991, abandoned.

[51] Int. Cl.$^6$ ..................... A61K 31/165; C07C 233/65
[52] U.S. Cl. .................. 514/619; 564/163; 564/166
[58] Field of Search ................................ 564/163, 164, 564/166; 514/619, 620

[56] References Cited

U.S. PATENT DOCUMENTS

| | | | |
|---|---|---|---|
| 3,974,289 | 8/1976 | Buckle et al. | 424/281 |
| 4,012,407 | 3/1977 | Doyle et al. | 260/465 R |
| 4,032,544 | 6/1977 | Doyle et al. | 260/343.2 |
| 4,737,517 | 4/1988 | DellaValle et al. | 514/457 |
| 4,845,121 | 7/1989 | Witiak et al. | 514/455 |

FOREIGN PATENT DOCUMENTS

| | | | |
|---|---|---|---|
| 0371560 | 6/1990 | European Pat. Off. | A01N 43/04 |
| 3-227923 | 1/1990 | Japan | A61K 31/37 |
| 2036017 | 6/1980 | United Kingdom | A61K 31/35 |
| 2244646 | 11/1991 | United Kingdom | A61K 31/165 |
| WO89/07441 | 8/1989 | WIPO | A61K 31/35 |
| WO89/07939 | 9/1989 | WIPO | A61K 31/37 |

OTHER PUBLICATIONS

Rice, W. et al., "Induction of endonuclease–mediated apoptosis in tumor cells by C–nitroso–substituted ligands of poly (ADP–ribose) polymerase." Proc. Natl. Acad. Sci. 89 7703–7707 (1992).

Buki, K. et al., "Destabilization of $Zn^{2+}$ coordination in ADP–ribose transferase (polymerizing) by C–nitroso–1, 2–benzopyrone coincidental with inactivation of the polymerase but not the DNA binding function," FEBS 290: 181–185 (1991).

Kirsten, E. et al., "Cellular regulation of ADP–ribosylation of proteins IV. Conversion of poly (ADP–Ribose) polymerase activity to NAD–glycohydrolase during retinoic acid–induced differentiation of HL60 cells." Experimental Cell Research 194:1–8 (1991).

Buki, K. et al., "Inhibitor binding of adenosine disphophoribosyl transferase to the DNA primer site of reverse transcriptase templates." Biochem. Biophys. Res. Com. 180:496–503 (1991).

Cole, G. et al., "Inhibition of HIV–1 IIIb replication in AA–2 and MT–2 cells in culture by two ligands of poly (ADP–ribose) polymerase: 6–amino–1,2–benzopyrone and 5–iodo–6–amino–1,2–benzopyrone." Biochem. Biophys. Res. Com. 180:504–514 (1991).

Henderson, L. et al., "Primary structure of the low molecular weight nucleic acid–binding proteins of murine leukemia viruses" J. Biol. Chem. 256(16) 8400–8403 (1981).

Gorelick, R. et al., "Point mutants of moloney murine leukemia virus that fail to package viral RNA: evidence for specific RNA recognition by a zinc–finger like" protein sequence, Proc. Natl. Acad. Sci 85:8420–8424 (1988).

Gorelick, R. et al., "Noninfectious human immunodeficiency virus Type 1 mutants deficient in genomic RNA." J. Virol. 64:3207–3211 (1990).

Meric, C. et al., "Characterization of moloney murine leukemia virus mutants with single amino acid substitutions in the Cys–His box of the nucleocapsid protein." J. Virol. 63:1558–1568 (1989).

Aldovini, A. et al., "Mutations of RNA and protein sequences involved in human immunodeficiency virus Type I packaging result in production of noninfectious virus." J. Virol 64:1920–1926 (1990).

Lever, A. et al., "Identification of a sequence required for efficient packaging of human immunodeficiency virus Type I RNA into virions." J. Virol 63:4085–4087 (1989).

Gradwohl, G. et al., "The second zinc–finger domain of poly (ADP–ribose) polymerase determines specificity for single–stranded breaks in DNA." Proc. Natl. Acad. Sci. 87 2990–2994 (1990).

South, T. et al., "113 Cd NMR studies of 1:1 Cd adduct with an 18–residue finger peptide from HIV–1 nucleic acid binding protein, p. 7." J. Am. Chem. Soc. 111 395–396 (1989).

South, T. et al., "Zinc fingers and molecular recognition. Structure and nucleic acid binding studies of an HIV zinc fingerlike domain." Biochem. Pharm. 40:123–129 (1990).

Summers, M. et al., "High–resolution structure of an HIV zinc fingerlike domain via a new NMR–based distance geometry approach." Biochemistry 29:329–340 (1990).

Yamagoe, S. et al., "Poly (ADP–ribose) polymerase inhibitors suppress UV–induced human immunodeficiency virus type 1 gene expression at the posttranscriptional level." Molecular and Cellular Biology 11(7) 3522–3527 (1991).

Krasil'Nikov, I. et al., "Inhibitors of ADP–ribosylation as antiviral drugs: Experimental study of the model of HIV infection." VOPR. Virusol (Russia) 36(3) 216–218 (1991).

Furlini, G. et al., "Increased poly (ADP–ribose) polymerase (List continued on next page.)

Primary Examiner—Shailendra Kumar
Attorney, Agent, or Firm—Albert P. Halluin; Scott R. Bortner; Pennie & Edmonds

[57] ABSTRACT

The subject invention provides for novel compounds for inactivating viruses. These compounds include 6-nitroso-1, 2-benzopyrone, 3-nitrosobenzamide, 5-nitroso-1(2H)-isoquinolinone, 7-nitroso-1(2H)isoquinolinone, 8-nitroso-1(2H)isoquinolinone. The invention also provides for compositions containing one or more of the compounds, and for methods of treating viral infections, cancer, infectious virus concentration with the subject compounds and compositions.

2 Claims, 16 Drawing Sheets

OTHER PUBLICATIONS activity in cells infected by human immunodeficiency virus type–1." Microbiologica 14(2) 141–148 (1991).

Ibna–Rasa, K. et al., "O–Nitrosobenzamide. A possible intermediate in the von Richter reaction." J. Org. Chem. 28(11) 3240–3241, 1963.

Seidel, W. et al., "Oxidation of aromatic hydrazides." Chemical Abstracts 82 82 Col. 16505X (1975).

Wubbels, G. et a., "Mechanism of water–catalyzed photo–isomerization of p–nitrobenzaldehye." J. Org. Chem. 47(24) 4664–4670 (1982).

Kovacic, P. et al., "Reduction potentials in relation to physiological activities of benzenoid and heterocyclic nitroso compounds: comparison with the nitro precursors," Bioorganic Chemistry 18: 265–275 (1990).

Ehlhardt, W. J. et al., "Nitrosoimidazoles: highly bactericidal analogues of 5–nitroimidazole drugs." J. Med. Chem. 31: 323–329 (1988).

McClelland, R. A. et al., "Products of the reductions of 2–nitroimidizoles." J. Am. Chem. Soc. 109: 4308–4314 (1987).

Noss, M. B. et al., "Preparation, toxicity and mutagenicity of 1–methyl–2–nitrosoimidazole." Biochem. Pharm. 37: 2585–2593 (1988).

Varghese, A. J. et al., "Modification of guanine derivatives by reduced 2–nitroimidazoles." Cancer Research 43: 78–82 (1983).

Buki, K. et al., "Destabilization of Zn(II) coordination in poly(ADP–Ribose) polymerase by 6–nitroso–1, 2–benzopyrone coincidental with inactivation of the polymerase but not with the DNA binding function." The Paul Mandel International Meeting of Poly (ADP–Ribosyl)ation Reactions. Abstract 22C May 30, 1991.

Mulcahy, R. T. et al., "Cytotoxicity and glutathione depletioni by I–methyl–2–nitrosoimidazole in human colon cancer cells." Biochem. Pharm. 38: 1667–1671 (1989).

Noss, M. B. et al., "I–Methyl–2–nitrosoimidazole: cytotoxic and glutathione depleting capabilities." Int. J. Radiation Oncology Biol. Phys. 16: 1015–1019 (1989).

ADENOSINE DIPHOSPHORIBOSE POLYMERASE BINDING NITROSO AROMATIC COMPOUNDS USEFUL AS RETROVIRAL INACTIVATING AGENTS, ANTI-RETROVIRAL AGENTS AND ANTI-TUMOR AGENTS

CROSS REFERENCE TO RELATED APPLICATIONS

This application is a continuation in part of copending application Ser. No. 07/893,429 filed Jun. 4, 1992, abandoned which is a continuation in part of application Ser. No. 07/780,809, filed Oct. 22, 1991, now abandoned.

FIELD OF THE INVENTION

The present invention relates generally to the field of retroviral therapeutic and inactivating agents and their use in treating retroviral infections and cancers. More specifically it relates to those therapeutic and inactivating C-nitroso compounds which destabilize zinc fingers.

BACKGROUND OF THE INVENTION

The enzyme ADP-ribose transferase (ADPRT) (E.C.4.2.30) is a chromatin-bound enzyme located in the nucleus of most eukaryotic cells. The enzyme catalyzes the polymerization of the ADP-ribose moiety of nicotinamide adenine dinucleotide ($NAD^+$) to form poly (ADP-ribose). The polymer is covalently attached to various nuclear proteins, including the polymerase itself.

The many varied roles that ADP-ribosylation plays in cellular metabolism have made ADPRT a target for drugs essentially useful for combating neoplasia and viral infections. Numerous physiological activities have been detected for compounds that inhibit the polymerase activity of ADPRT. Such activities include a cell cycle dependent prevention of carcinogen-induced malignant transformation of human fibroblasts (Kun, E., Kirsten, E., Milo, G. E. Kurian, P. and Kumari, H. L. (1983) *Proc. Natl. Acad. Sci. USA* 80:7219–7223), conferring also carcinogen resistance (Milo, G. E., Kurian, P., Kirsten, E. and Kun, E. (1985) *FEBS Lett.* 179:332–336), inhibition of malignant transformation in hamster embryo and mouse C3H10T1/2 cell cultures (Borek, C., Morgan, W. F., Ong, A. and Cleaver, J. E. (1984) *Proc. Natl, Acad. Sci. USA* 81:243–247), deletion of transfected oncogenes from NIH 3T3 cells (Nakayashu, M., Shima, H., Aonuma, S., Nakagama, H., Nagao. M. and Sugimara, T. (1988) *Proc. Natl. Acad. Sci. USA* 85:9066–9070), suppression of the mitogenic stimulation of tumor promoters (Romano, F., Menapace, L. and Armato, V. (1983) *Carcinogenesis* 9:2147–2154), inhibition of illegitimate DNA recombinations (Waldman, B. C. and Waldman, A. (1990) *Nucl. Acids Res.* 18:5981–5988) and integration (Farzaneh, F., Panayotou, G. N., Bowler, L. D., Hardas, B. D., Broom, T., Walther, C. and Shall, S. (1988) *Nucl. Acids Res.* 16:11319–11326), induction of sister chromatid exchange (Ikushima, T. (1990) *Chromosoma* 99:360–364) and the loss of certain amplified oncogenes (Grosso, L. E. and Pitot, H. C. (1984) *Biochem. Biophys. Res Commun.* 119:473–480; Shima, H., Nakayasu, M., Aonums, S., Sugimura, T. and Nagao, M. (1989) *Proc. Natl. Acad. Sci. USA* 86:7442–7445).

Compounds known to inhibit ADPRT polymerase activity include benzamide (Kun, E., Kirsten, E., Milo, G. E. Kurian, P. and Kumari, H. L. (1983) *Proc. Natl, Acad. Sci. USA* 80:7219–7223), substituted benzamides (Borek, C., Morgan, W. F., Ong, A. and Cleaver, J. E. (1984) *Proc. Natl. Acad. Sci. USA* 81:243–247; Romano, F., Menapace, L. and Armato, V. (1983) *Carcinogenesis* 9; 2147–2154; Farzaneh, F., Panayotou, G. N., Bowler, L. D., Hardas, B. D., Broom, T., Walther, C. and Shall, S. (1988) *Nucl. Acids Res.* 16:11319–11326.; Grosso, L. E. and. Pitot, H. C. (1984) *Biochem. Biophys. Res. Commun.* 119:473–480; Shima, H., Nakayasu, M., Aonums, S., Sugimura, T. and Nagao, M. (1989) *Proc. Natl. Acad. Sci. USA* 86:7442–7445), 3-aminonaphthylhydrazide (Waldman, B. C. and Waldman, A. (1990) *Nucl. Acids. Res.* 18:5981–5988), isoquinoline, quercetin, and coumarin (1,2-benzopyrone) (Milo, G. E., Kurian, P., Kirsten, E. and Kun, E. (1985) *FEBS Lett.* 179:332–336). The anti-transforming and anti-neoplastic effect of 1,2 benzopyrone were demonstrated in vitro and in vivo (Tseng, et al., (1987) *Proc. Natl, Acad. Sci. USA* 84:1107–1111).

Other known ADPRT polymerase activity inhibitors include 5-iodo-6-amino-1,2-benzopyrone as described in U.S. patent application Ser. No. 600,593, filed Oct. 19, 1990 entitled "Novel 5-Iodo-6-Amino-1,2-Benzopyrones and their Metabolites Useful as Cystostatic and Anti-Viral Agents" for use as anti-tumor and anti-viral agents. The cited patent discusses the possibility of using 5-iodo-6-nitroso-1,2-benzopyrone as an anti-tumor or anti-viral agent.

The 6-nitroso-benzopyrones have not been hitherto known or described. The only remotely related compounds found in the literature are 6-nitro-1,2-benzopyrone and 6-amino-1,2-benzopyrone (6-ABP) (*J. Pharm. Soc. Jap.*, 498:615 (1923)) for which, only scarce medicinal evaluation has been reported. In particular, testing was done for sedative and hypnotic effects (*J. Pharm. Soc. Japan*, 73:351 (1953); Ibid, 74:271 (1954)), hypothermal action (*Yakugaku Zasshi*, 78:491 (1958)), and antipyretic, hypnotic, hypotensive and adrenolytic action (Ibid, 83:1124 (1963)). No significant application for any of these compounds has been described except for 6-ABP.

2-nitrosobenzamide (Irne-Rasa, K. M. and Koubek, E. (1963) *J. Org. Chem.* 28:3240–3241), and 4-nitrosobenzamide (Wubbels, G. G., Kalhorn, T. F., Johnson, D. E. and Campbell, D. (1982) *J. Org. Chem.* 47:4664–4670), have been reported in the chemical literature, but no commercial use of these isomers is known. Neither of these articles suggest the use of nitrosobenzamides as ADPRT inhibitors.

The anti-retroviral and anti-tumorigenic actions of substituted and unsubstituted 6-amino- 1,2-benzopyrone and 5-iodo-6-amino-1,2-benzopyrone is the subject of copending U.S. patent applications Ser. No. 585,231 filed on Sep. 21, 1990 entitled "6-Amino-1,2-Benzopyrones Useful for Treatment of Viral Diseases" and Ser. No. 600,593 filed on Oct. 19, 1990 entitled "Novel 5-Iodo-6-Amino-1,2-Benzopyrones and Their Metabolites Useful as Cytostatic and Antiviral Agents", which are incorporated herein by reference.

The precursor molecule, 1,2-benzopyrone (coumarin), was shown to be an inhibitory ligand of adenosinediphosphoribosyl transferase (ADPRT), a DNA-binding nuclear protein present in all mammalian cells (Tseng, et al., (1987) *Proc. Nat. Acad. Sci. USA*, 84:1107–1111).

Hakam, et al., *FEBS Lett.*, 212:73 (1987) has shown that 6-amino-1,2-benzopyrone (6-ABP) binds specifically to ADRPT at the site that also binds to DNA, indicating that both 6-ABP and DNA compete for the same site on ADPRT. Synthetic ligands of ADPRT inhibit DNA proliferation, particularly in tumorigenic cells, (Kirsten, et al., (1991) *Exp. Cell. Res.* 193:1–4). Subsequently, these ligands were found to inhibit viral replication and are the subject of the copending U.S. patent application entitled "6-Amino-1-2-Benzopyrones useful for Treatment of Viral Diseases," Ser. No. 585,231, filed on Sep. 21, 1990 which is hereby incorporated by reference.

Retroviral nucleocapsid (NC) proteins and their respective gag precursors from all strains of known retroviruses contain at least one copy of a zinc-binding polypeptide sequence of the type $Cys-X_2-Cys-X_4-His-X_4-Cys$ (CCHC) (Henderson, et al., *Biol. Chem,* 256:8400–8406 (1981)), i.e., a zinc finger domain. This CCHC sequence is essential for maintaining retroviral infectivity (Gorelick, et al., *Proc. Natl. Acad. Sci. USA* 85:8420–8424 (1988), Gorelick, et al., *J. Virol.* 64:3207–3211 (1990)), therefore, it represents an attractive target for retroviral chemotherapy. The HIV-1 gag proteins function by specifically binding to the HIV-1 RNA, anchoring it to the cell membrane for budding or viral particles (Meric, et al., *J. Virol.* 63:1558–1658 (1989) Gorelick, et al., *Proc. Natl. Acad. Sci. USA* 85:8420–8424 (1988), Aldovini, et al., *J. Virol.* 64:1920–1926 (1990), Lever, et al., *J. Virol,* 63:4085–4087 (1989)). Site-directed mutagenesis studies demonstrated that modification of Cys or His residues results in defective viral RNA packaging and noninfectious viral particles are formed (Aldovini, et al., *J. Virol.* 64:1920–1926 (1990), Lever, et al., *J. Virol.* 63:4085–4087 (1989)). The highly abundant nonhistone nuclear protein of eukaryotes, poly(ADP-ribose) polymerase (E.C.2.4.4.30), also contains two CCHC-type zinc fingers located in the basic terminal polypeptide domain, as analyzed by site directed mutagenesis (Gradwohl, et al., *Proc. Natl. Sci. USA* 87:2990–2992 (1990)).

Published experiments have shown that aromatic C-nitroso ligands of poly (ADP-ribose) polymerase preferentially destabilize one of the two zinc fingers coincidental with a loss of enzymatic activity but not DNA binding capacity of the enzyme protein (Buki, et al., *FEBS Lett.* 290:181–185 (1991)). Based on the similarity to results obtained by site-directed mutagenesis (Gradwohl, et al., *Proc. Natl. Acad. Sci. USA* 87:2990–2992 (1990)), it appears that the primary attack of C-nitroso ligands occurred at zinc finger FI (Buki, et al., *FEBS Lett.* 290:181–185 (1991)). A selective cytocidal action of the C-nitroso group containing poly (ADP-ribose) polymerase ligands on cancer cells was subsequently discovered (Rice et al., *Proc. Natl. Acad. Sci. USA* 89:7703–7707.

Based on the coincidental occurrence of the CCHC type zinc fingers in both retroviral NC proteins and in poly(ADP-ribose) polymerase and the observed chemotherapeutic effects of C-nitroso-containing ligands on cancer cells, experiments were initiated to test if the C-nitroso compounds also have antiviral effects on retroviruses containing NC proteins. As described herein experiments testing this hypothesis with the polypeptide corresponding to the N-terminal CCHC zinc finger of HIV-1 NC protein, Zn(HIV1-F1) (South, et al., *Am. Chem. Soc.* 111:395–396 (1989), South, et al., *Biochem. Pharm.* 40:123–129 (1990), Summers, et al., *Biochemistry* 29:329–340 (1990)), intact HIV-1 virions and on the propagation of HIV-1 in human lymphocytes in culture, were performed.

SUMMARY OF THE INVENTION

The subject invention provides for novel anti-tumor compounds, anti-retroviral compounds and retroviral inactivating compounds. These compounds include 6-nitroso-1,2-benzopyrone, 3-nitrosobenzamide, 2-nitrosobenzamide, 4-nitrosobenzamide, 5-nitroso-1(2H)-isoquinolinone, 7-nitroso-1(2H)isoquinolinone, 8-nitroso-1(2H)isoquinolinone.

The invention also provides for compositions containing one or more of the compounds, and for methods of treating retroviral infections and cancer with these compounds and compositions.

Also provided for are methods of treating cancer and retroviral infections with 2-nitrosobenzamide, 3-nitrosobenzamide and 4-nitrosobenzamide. Compositions containing one or more of these compounds are also provided.

Another aspect of the invention is to provide methods for inactivating viruses, especially retroviruses, in biological materials, e.g., blood, by adding various nitroso compounds including 6-nitroso-1,2-benzopyrone, 2-nitrosobenzamide, 3nitrosobenzamide, 4-nitrosobenzamide, 5-nitroso-1(2H)-isoquinoline, 7-nitroso-1(2H)-isoquinoline and 8-nitroso-1(2H) isoquinoline.

An additional aspect of the subject invention is to provide novel compositions of biological materials comprising biological material and the compounds used in the subject methods.

DESCRIPTION OF THE FIGURES

FIG. 13 B. shows an HIV-1 inactivation assay using NOBA at different temperatures. The assay was performed as described in FIG. 13A except that the 30 min. preincubation of virus with NOBA was carried out at 0>, 22° or 37° C.

FIG. 13 C. shows the dose-responsive effect of NOBA on PHA-PBL viability. PHA-PBL (10$^6$/ml) were treated with increasing doses of NOBA for 24 hours in the presence of MTT substrate and the relative absorbance at 550 nm reflects the metabolic activity of the cells. The level of product formation in the absence of NOBA was considered to be 100% and all experimental values were normalized to that control value.

DESCRIPTION OF SPECIFIC EMBODIMENTS

Definitions

Figure 1:
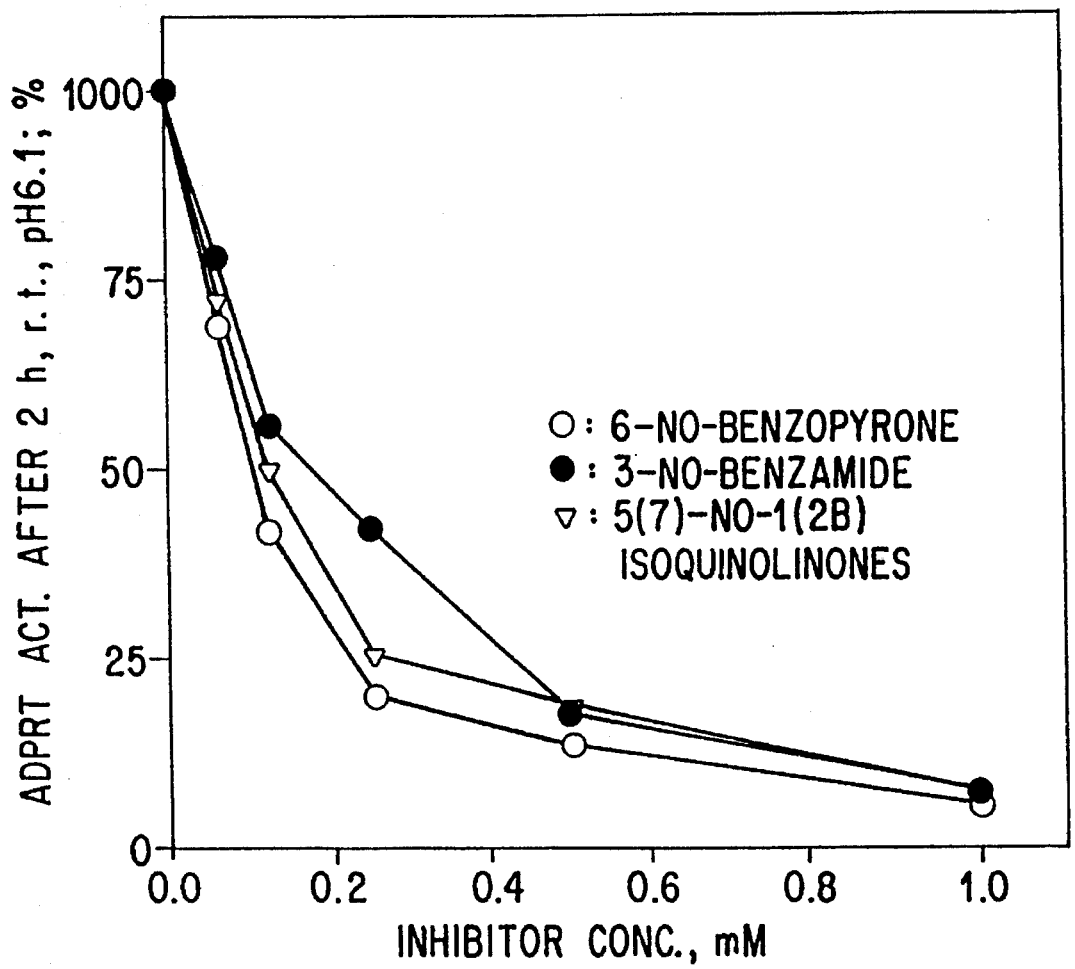
FIG. 1 is a graph comparing the degree of ADRPT polymerase activity (ADPRP) inactivation exhibited by different concentrations of 6-nitroso-1,2-benzopyrone, 3-nitroso-benzamide, and nitroso-1(2H)-isoquinolinones (NOQ) (a mixture of the 5 and 7 nitroso isomers).
Figure 2A:
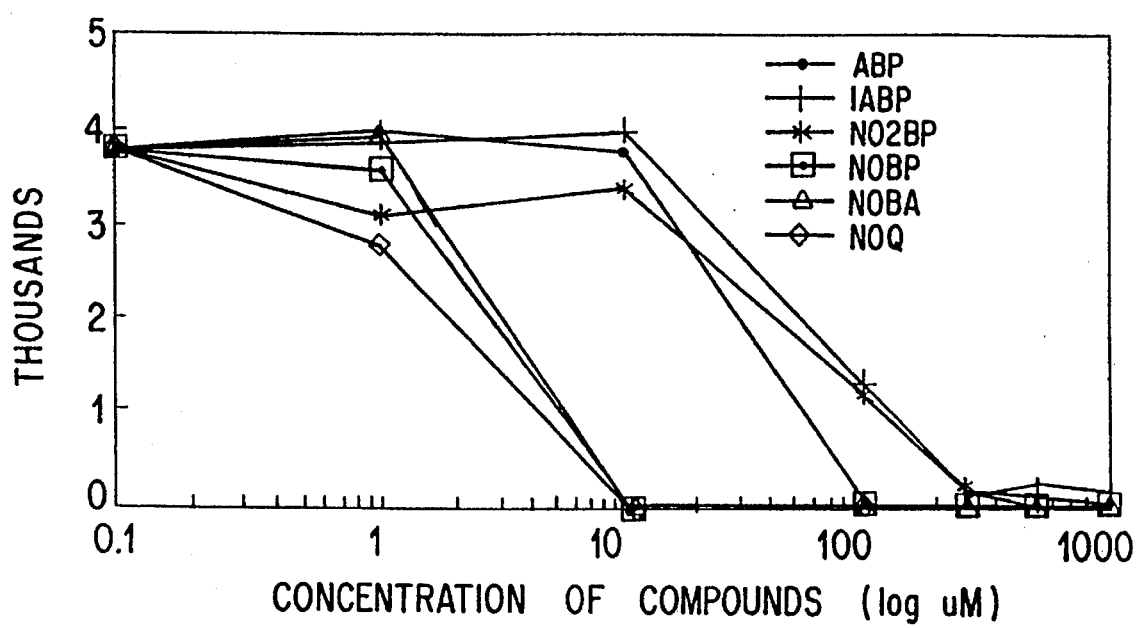
FIGS. 2A–2F are a composite of graphs displaying the inhibitory effects of the ADRPT ligands on (FIG. 2A) 855-2 cells (a cell line of human B-cell lineage acute lymphoblastic leukemia), (FIG. 2B) H9 cells (a cell line of human T-cell lineage acute lymphoblastic leukemia), FIG. (2C) HL-60 cells (a cell line of human acute nonlymphoblastic leukemia) and (FIG. 2D) K562 cells (a cell line of human chronic myelogenous leukemia). These cells were cultured while under the influence of the growth factors in 10% fetal bovine serum (FCS), whereas in (FIG. 2E) and (FIG. 2F) the 855-2 cells were cultured in the presence of autocrine growth factor activity (AGF) or low molecular weight-B-cell growth factor (BCGF, a T-cell derived lymphokine), respectively.
Figure 2B:
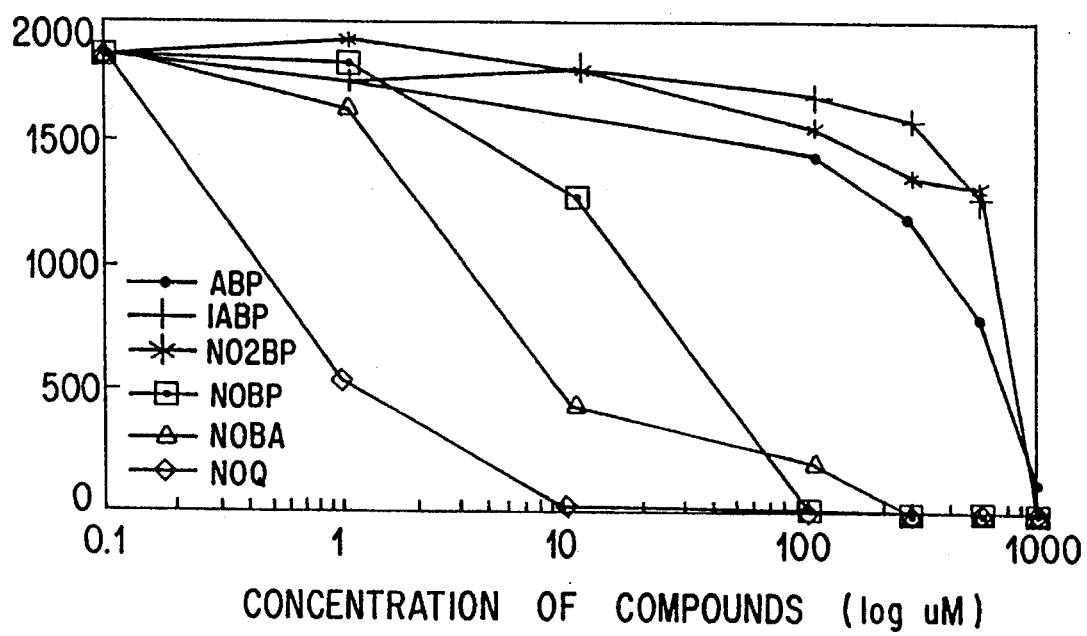
Figure 2C:
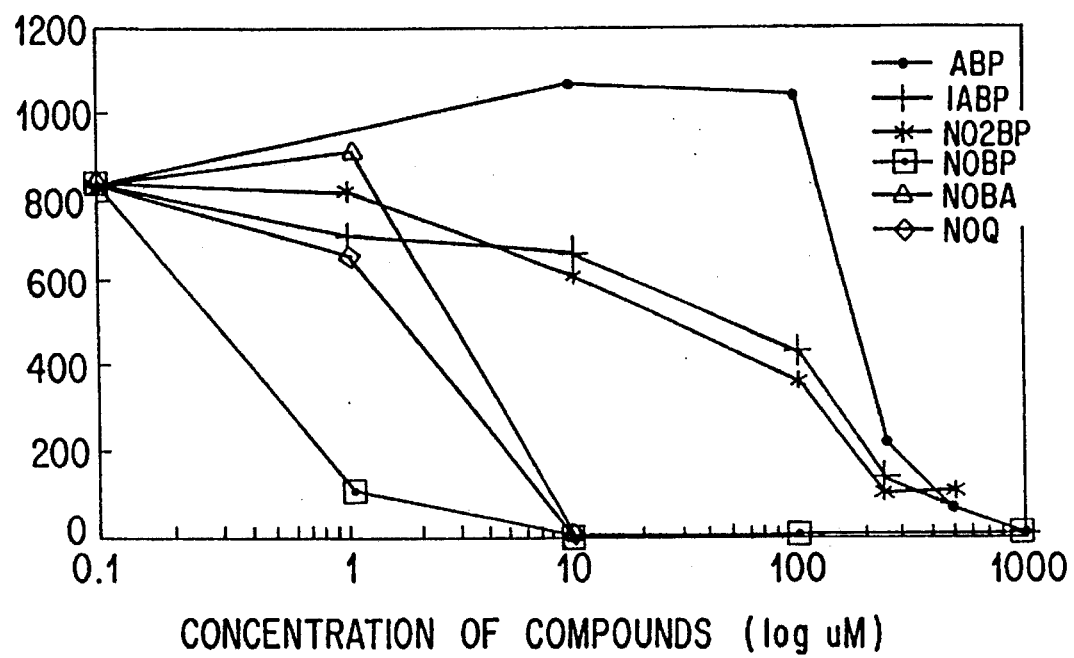
Figure 2D:
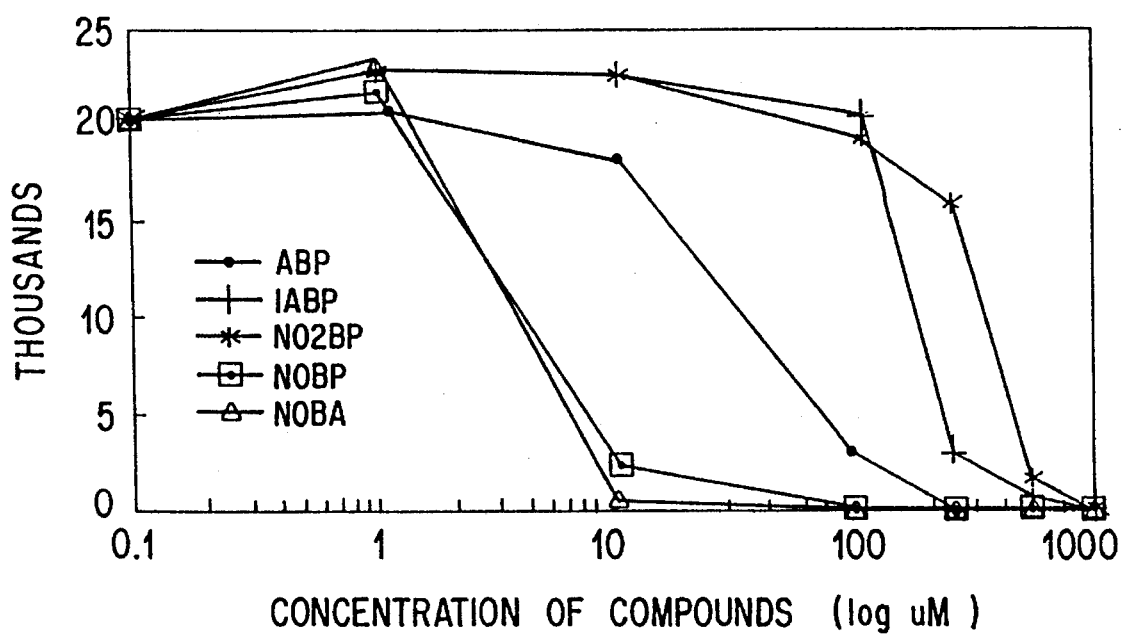
Figure 2E:
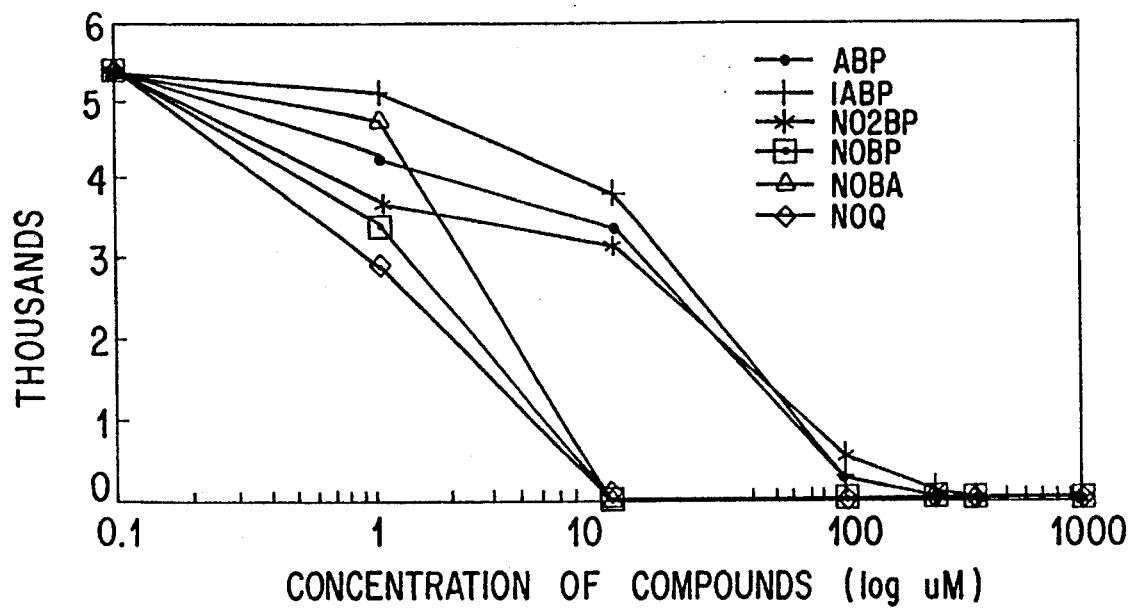
Figure 2F:
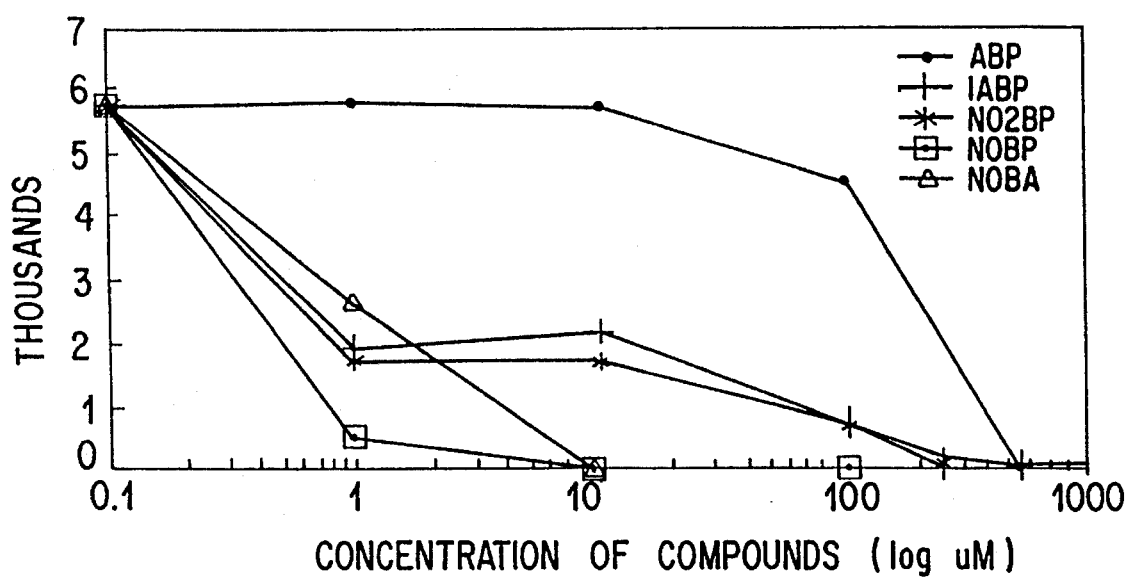

The term "biological material" as ued herein, refers to any biological material extracted from a living organism, including blood, plasma, cerebrospinal fluid, organs, and the like, as well as the processed products of biological material extracted from a living organism.

The term "biological composition" as used herein, refers to a composition comprising a biological material and a compound of interest.

The term "cancer" as used herein, refers to malignant tumors consisting of cells that do not follow normal control signals for proliferation or positioning.

The term "retrovirus" as used herein refers to RNA viruses which utilize the enzyme reverse transcriptase to trancribe infecting RNA chains into DNA complements.

The term "zinc finger" refers to a structural domain of a protein capable of binding a zinc atom. The nature of zinc finger proteins domains is well described in the literature, e.g., Klug and Rhodes, *Trends in Biochemical Sciences* 12:464–469 (1987).

The Invention

The subject invention provides for several nitroso compounds that are ADPRT polymerase activity inhibitors. These compounds find use as anti-tumor and antiviral compounds.

Compound (I) has the following formula:

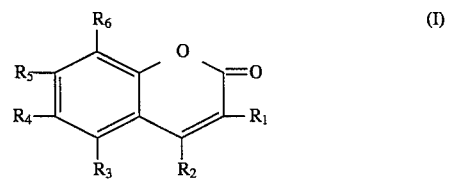

wherein R$_1$, R$_2$, R$_3$, R$_4$, R$_5$, and R$_6$ are selected from the group consisting of hydrogen and nitroso, and only one of R$_1$, R$_2$, R$_3$, R$_4$, R$_5$, and R$_6$ is a nitroso group.

A preferred embodiment of compound I is where R$_4$ is the nitroso group, i.e., the molecule 6-nitroso-1,2-benzopyrone.

Compound II has the formula:

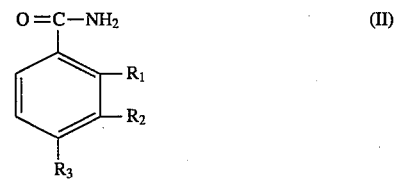

wherein R$_1$, R$_2$, and R$_3$ are selected from the group consisting of hydrogen and nitroso, and only one of R$_1$, R$_2$, and R$_3$ is a nitroso group.

Compound III has the formula:

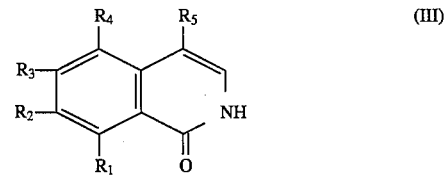

wherein R$_1$, R$_2$, R$_3$, R$_4$, and R$_5$ are selected from the group consisting of hydrogen and nitroso, and only one of R$_1$, R$_2$, R$_3$, R$_4$, and R$_5$ is a nitroso group.

Preferred embodiments of compound III are where either R$_2$ or R$_4$ is the nitroso group, i.e., 7-nitroso-1(2H)-isoquinolinone and 5-nitroso-1(2H)-isoquinolinone, respectively.

The disclosed synthesis for 5-nitroso-1(2H)-isoquinolinone may produce 2 closely related structural isomers, 7-nitroso- 1(2H)-isoquinolinone and 8-nitroso-1(2H)-isoquinolinone. Although experiments testing the biological activity of 5-nitroso-1(2H)-isoquinolinone may have contained significant quantities of 8-nitroso-1(2H)-isoquinolinone or 7-nitroso-1(2H)-isoquinolinone, all three isomers are believed to possess similar anti-tumor tumor and anti-viral activity on the basis of their close structural similarity. This hypothesis may be conveniently tested by separating the isomers by thin layer chromatography or similar methods, and comparing the anti-tumor and anti-viral activities of the separated compounds.

Detailed synthesis of 6-nitroso-1,2-benzopyrone, 3-nitroso-benzamide, 5-nitroso-1(2H)-isoquinolinone, 7-nitroso-1(2H)-isoquinolinone, and 8-nitroso-1(2H)-isoquinolinone, is provided in the example section below.

In general, the nitroso compounds of the subject of invention may be synthesized by oxidizing a corresponding amino compound to a compound of the subject invention by oxidation with 3-chloroperoxybenzoic acid (or other peroxyacids) in ethyl acetate, a halocarbon solvent or in a relatively concentrated solution in dimethyl formamide.

Detailed synthesis of 3-nitrosobenzamide is described in the example section below. Synthesis of the other precursor amino compounds are described in the chemical literature. Some of the compounds are commercially available. Some precursor amino compounds for oxidation to nitroso compounds of the subject invention are as follows: 3-amino-1,2-benzopyrone (Spectrum Chemical Mfg. Corp., Gardena, Calif. 90248); 4-amino-1,2-benzopyrone (Aldrich, Rare Chemical Catalog); 5-amino-1,2-benzopyrone (by reduction of 5-nitro- 1,2-benzopyrone, *Chem. Abst.* 57 16536d (1962)); 7-amino-1,2-benzopyrone (Gottlieb, et al., *J. Chem. Soc. Perkin. Trans. II* 435 (1979)); 8-amino-1,2-benzopyrone (by reduction of 8-amino-1,2-benzopyrone, Abdel-Megid, et al., *Egypt J. Chem.* 20:453–462 (1977)), and 4-amino-1(2H)-isoquinolinone, by reduction of the corresponding 4-nitro analog (Horning, et al., (1971) *Can. J. Chem.* 49:2785–2796).

In addition to compounds (I) to (III), the subject invention contemplates various structurally related compounds that have similar carcinostatic and/or anti-viral activities. These structurally related compounds could be conveniently screened on the basis of their highly potent inhibitory effect on ADPRT polymerase activity. Structurally related compounds of interest include derivatives substituted by additional nitroso groups and small, e.g., $C_1$–$C_3$ alkyl groups. Also of interest are various nitroso substituted structurally related heterocyclic rings such as 3,4-dihydro-1(2H)-isoquinolinones, nicotinamides, pthalhydrazides, and 1,3-benzoxazine-2,4-diones.

Another aspect of the compounds of the subject invention are the ease with which they permeate cell membranes and their relative absence of non-specific binding to proteins and nucleic acid.

In practice, the ADPRT polymerase inhibitors of this invention, namely compounds (I) to (III), and any of their pharmaceutically acceptable salts, may be administered in amounts, either alone or in combination with each other, and in the pharmaceutical form which will be sufficient and effective to inhibit neoplastic growth or viral replication or prevent the development of the cancerous growth or viral infection in the mammalian host.

Administration of the active compounds and salts described herein can be via any of the accepted modes of administration for therapeutic agents. These methods include systemic or local administration such as oral, parenteral, transdermal, subcutaneous, or topical administration modes. The preferred method of administration of these drugs is intravenous, except in those cases where the subject has topical tumors or lesions, where the topical administration may be proper. In other instances, it may be necessary to administer the composition in other parenteral or even oral forms.

Depending on the intended mode, the compositions may be in the solid, semi-solid or liquid dosage form, such as, for example, injectables, tablets, suppositories, pills, time-release capsules, powders, liquids, suspensions, or the like, preferably in unit dosages. The compositions will include an effective amount of at least one of compounds (I) to (III), or pharmaceutically acceptable salts thereof, and in addition it may include any conventional pharmaceutical excipients and other medicinal or pharmaceutical drugs or agents, carriers, adjuvants, diluents, etc., as customary in the pharmaceutical sciences.

For solid compositions, in addition to the compounds (I) to (III), such excipients as, for example, pharmaceutical grades of mannitol, lactose, starch, magnesium stearate, sodium saccharin, talcum, cellulose, glucose, sucrose, magnesium carbonate, and the like may be used. The compounds of the subject invention may be also formulated as suppositories using, for example, polyalkylene glycols, for example, propylene glycol, as the carrier.

Liquid, particularly injectable compositions can, for example, be prepared by dissolving, dispersing, etc., at least one of active compounds (I) to (III) in a pharmaceutical solution such as, for example, water, saline, aqueous dextrose, glycerol, ethanol, DMSO and the like, to thereby form the injectable solution or suspension.

If desired, the pharmaceutical composition to be administered may also contain minor amounts of nontoxic auxiliary substances such as wetting or emulsifying agents, pH buffering agents, and other substances such as, for example, sodium acetate, triethanolamine oleate, etc.

Parenteral injectable administration is generally used for subcutaneous, intramuscular or intravenous injections and infusions.

Injectables can be prepared in conventional forms, either as liquid solutions or suspensions or solid forms suitable for dissolving in liquid prior to injection.

A more recently devised approach for parenteral administration employs the implantation of a slow-release or sustained-release systems, which assures that a constant level of dosage is maintained, according to U.S. Pat. No. 3,710,795, which is incorporated herein by reference.

Any of the above pharmaceutical compositions may contain 0.01–99%, preferably 1–70% of the active ingredient.

Actual methods of preparing such dosage forms are known, or will be apparent to those skilled in this art, and are described in detail in *Remington's Pharmaceutical Sciences*, Mack Publishing Company, Easton, Pa., 17th Edition, 1985. The composition or formulation to be administered will, in any event, contain such quantity of the active compound(s) that will assure that a therapeutically effective amount will be delivered to a patient. A therapeutically effective amount means an amount effective to prevent development of or to alleviate the existing symptoms of the subject being treated.

The amount of active compound administered will, of course, be dependent on the subject being treated, on the subject's weight, the severity of the affliction, the manner of administration and the judgment of the prescribing physician. However, an effective dosage may be in the range of 1 to 12 mg/kg/day, preferably 1 to 5 mg/kg/day, given only for 1–2 days at one treatment cycle. Generally, the upper limit for the drug dose determination is its efficacy balanced with its possible toxicity.

The subject invention provides for methods of reducing the titer of infectious retroviruses, particularly retroviruses (including the retrovirus HIV-1) in biological materials by inactivating the viruses. Viruses may be inactivated by contact between the compound of interest and the virus. The term "reducing" includes the complete elimination of all the infectious viruses of interest, as well as a diminution in the titer of the infectious viruses. It is of particular interest to reduce the number of infectious viruses in biological material that is to be introduced into a living organism so as to reduce the possibility for infection. It is also of interest to reduce the titer infectious viruses that might be present in or on non-biological materials that come into contact with living organisms, such non-biological materials include surgical instruments, dental instruments, hypodermic needles, public sanitary facilities, and the like.

A preferred embodiment of the subject invention is the reduction in infectious virus concentration in blood.

Although the effective amount of the viral-inactivating compound used in the subject method will vary in accordance with the nature of the compound and the particular material, biological or otherwise of interest, a preferred concentration of 3-nitrosobenzamide is about 15 micromolar. An effective amount may readily be determined by testing the effect of a range of concentrations of the compound of interest on the viral titer of a composition containing a virus of interest.

The subject methods of reducing infectious virus concentration in biological materials inactivate viruses by employing the step of adding an effective amount of compounds I, II or III,or combinations thereof. These nitroso compounds can destabilize $Zn^{+2}$ fingers, i.e. eject $Zn^{+2}$ of the nucleocapsid proteins of viruses, particularly retroviruses. Preferred embodiments of compounds I, II and III for use in inactivating viruses are 6-nitroso-1,2-benzopyrone, 3-nitrosobenzamide, 5-nitroso-1(2H)-isoquinoline, 7-nitroso-1(2H)-isoquinoline, 8-nitroso-1(2H)-isoquinoline, and 3-nitrosobenzamide. The use of 3-nitroso benzamide is particularly preferred.

Another aspect of the invention is to provide for novel compositions consisting of biological materials containing an effective amount of nitroso compounds I, II and III, or combinations thereof. Preferred embodiments of compounds I, II and III for use in the subject composition are 6-nitroso-1,2-benzopyrone, 3-nitrosobenzamide, 5-nitroso-1(2H)-isoquinoline, 7-nitroso-1(2H)-isoquinoline, 8-nitroso- 1(2H)-isoquinoline, 2-nitrosobenzamide, 4-nitrosobenzamide, and 3-nitrosobenzamide. The use of 3-nitrosobenzamide is particularly preferred. The subject biological compositions may have diminished viral concentrations and may thus be administered with less risk of infection than comparable biological materials.

The subject invention also provides for methods of detecting compounds that can inactivate viruses, particular retroviruses, by testing for the effect of $Zn^{+2}$ finger destabilizing, i.e. $Zn^{+2}$ ejecting, compounds on the titer of a virus. Virus titer may be measured by well known methods suitable for measuring the titer of a virus of interest. The ejection of $Zn^{+2}$ from a zinc finger domain may be measured, among other methods, by NMR and/or $^{65}Zn^{+2}$ as described herein and as described in Buki, et al., *FEBS Lett.*, 290:181–185 (1991).

The invention having been described, the following examples are offered to illustrate the subject invention by way of illustration, not by way of limitation.

EXAMPLES

I. Synthesis and Characterization of 6-Nitroso-1,2-Benzopyrone

An example of a method for the preparation of 6-nitroso-1,2-benzopyrones is provided as follows:

To a stirred solution of 6 -amino-1,2-benzopyrone hydrochloride (4.00 g, 20 mmol) in water (40 ml) at 22° C. was added a solution of sodium tungstate (5.93 g, 20 mmol) in water (20 ml) followed by 30% aqueous hydrogen peroxide (5 ml) and stirring was continued for 1.5 hours. The oxidation product was extracted from the green-colored mixture with two 100 ml volumes of ethyl acetate, the combined extracts washed with 0.1N HCl (50 ml) and then water (100 ml). The ethyl acetate was removed by rotary evaporation and the residue recrystallized from warm ethanol (250 ml ).

Analysis of Reaction Product

The green crystals obtained from the recrystallization step (1.48 g, 42% yield) displayed-light absorption at 750 nm characteristic of monomeric arylnitroso compounds. Mass spectrum: m/z (relative intensity): 175 ($M^+$, 100), 161 (16.88), 145 (33.77), 133 (10.38), 117 (56.09), 89 (79.71), 63 (57.13). High resolution data for the $M^+$ peak: calculated for $C_9H_5NO_3$: 175.0268; found: 175.0271 (deviation—1.1 ppm). $^1$H-NMR ($CDCl_3$, 300 MHz) δ (ppm) from TMS: doublet (6.572 and 6.604) H-4 split by H-3; doublet (7,472 and 7,501) H-8 split by H-7; doublet of doublets (7.860/ 7.866 and 7.889/7.798) H-7 split by H- 8 and finely split by H-5; doublet (7.910 and 7.942) H-3 split by H-4; doublet (8.308 and 8.315) H-5 finely split by H-7. UV/VIS spectrum in ethanol, λ max (ε): 750 nm (46), 316 run ($8.96 \times 10^3$), 274 nm ($2.24 \times 10^4$). Melting Point: The compound polymerizes above 160° C., blackens and melts in the range of 325°–340° C.

This nitroso-compound may also be prepared by reacting 6-amino-1,2-benzopyrone (as the free base) with 3-chloroperoxybenzoic acid in ethyl acetate or halocarbon solvents.

II. Synthesis of 3-nitrosobenzamide

To a stirred solution of 3-aminobenzamide (Aldrich Chemical Co.) (0.476 g, 3.50 mmol) in ethyl acetate (50 ml) at ambient temperature was added 1.208 g of 3-chloroperoxybenzoic acid (commercial grade, 50–60% purity, Aldrich), whereupon the solution turned green. After 10 minutes the mixture was extracted with 0.14 M aqueous sodium bicarbonate (58 ml), washed with three successive 40-ml portions of water, dried over sodium sulfate, then reduced in volume to 20 mL by rotary evaporation and placed in the freezer (−20° C.), whereupon the product slowly deposited as a light yellow solid during a period of 72 hours (0.180 g, 34% yield).

The 2-nitrosobenzamide and 4-nitrosobenzamide isomers may be similarly prepared by oxididizing 2-aminobenzamide and 4-aminobenzamide, respectively.

Analysis of Reaction Product

Melting point: The substance darkens above 135° C., softens and apparently polymerizes in the range 150°–160° C., and melts at 240°–250° C. (with decomposition). In solution the compound is green-blue. Mass spectrum: m/z (relative intensity): 150 ($M^+$,100), 136 (10.9), 120 (77.2), 103 (31.6), 92 (46.5), 85 (22.8), 71 (33.3). High resolution data for the $M^+$ peak: calculated for $C_7H_6N_2O_2$:150.042928; found: 150.042900 (deviation=0.2 ppm). NMR spectrum: 1H-NMR (DMSO-$d_6$, 300 MHz) δ (ppm) from TMS: broad singlet (7.737)N-H; t (7.824, 7.850, 7.875) H-5 split by H-4 and H-6; d (8,059 and 8,086) H-6 split by H-5; d (8.357 and 8.383) H-4 split by H-5; s (8.472) H-2. The singlet at 7.737 corresponds to 1 proton; the second N-H proton, spectrally non-equivalent in this compound, is overlaid by the doublet of H-4. This doublet integrates to 2 protons and can be resolved by addition of $D_2O$ to the DMSO solution. UV-VIS absorption spectrum in absolute ethanol, λmax (ε):750nm (37.6), 304 nm (5.35×10hu 3) and 218 nm (1.50×10$^4$). An absorption maximum at 750 nm is characteristic of monomeric arylnitroso compounds.

In another embodiment, 3-nitrosobenzamide is synthesized by dissolving 3-aminobenzamide (5.0 g.) in N,N-dimethylformamide (DMF) solvent (25 ml) and then chilled in an ice bath. 3-Chloroperoxybenzoic acid (2.1 equivalents) is also dissolved in DMF solvent (25 ml) in a 250-ml flask equipped with a stirrer and thermometer and, as needed, an ice bath. This solution is chilled to 0°882–5° C., the ice bath is removed, and to it, with stirring, is added all at once the chilled 3-aminobenzamide solution. The mixture immediately becomes a transparent brown color, but within 0.5 minute turns to a deep green, and within 1.0 minute the temperature rises to 70° C., at which time the ice bath is reapplied to the reaction flask whereupon the temperature begins to fall, and is allowed to fall to 25° C., and stirring is continued for a total of 5 minutes. Some precipitation occurs (3,3'-azoxybenzamide side-product), thereafter the mixture is chilled to 5° C. for 10 minutes. The chilled mixture is filtered (suction) to remove the azoxy precipitate, and the green filtrate is poured into chilled (5°–10° C.) and stirred aqueous 0.40M Na$_2$CO$_3$ (200 ml), resulting in a light green suspension, and the suspension is stirred for an additional 10 minutes at 5°–10° C. to assure maximal product precipitation. Note that the pH of the suspension is about 8.5, which assures that 3-chlorobenzoic acid is retained in the aqueous solution as the sodium salt. The precipitate is then collected on a suction funnel and rinsed with deionized water (100 ml). This material, which is 3-NOBA (mostly as the tan dimer) containing residual 3,3'-azoxybenzamide side-product impurity, is then transferred, while damp, to a suitable flask and to it is added 50% aqueous acetic acid (200 ml). The mixture is warmed to 65°–70° C. to dissolve the dimer into the soluble monomeric 3-NOBA (green) and stirred for 5 minutes at 65° C.. The azoxy impurity (yellow) is poorly soluble and remains undissolved. The warm mixture is filtered (gravity) to give a clear green filtrate, which is allowed to cool. It is then chilled and placed in the refrigerator freezer (−20° C.) overnight to allow the 3-NOBA to redeposit as the light tan solid dimer. On the following day the solid product is collected on a suction filter, rinsed with fresh solvent, and the product cake is then dried by vacuum under mild warming for several hours. One typically obtains 2.24 g of dry 3-NOBA containing a trace of the azoxy impurity. The product is recrystallized by dissolving it again in 50% aqueous acetic acid (120 ml) and allowing to redeposit overnight in the freezer. After collection, rinsing and drying in vacuo, the weight is 2.08 g. (37% overall yield). TLC shows the material is 3-NOBA with a trace of the azoxy impurity.

III. Synthesis of Nitroso-1-(2H)-isoquinolinones (a mixture of 5-nitroso and 7-nitroso-isomers)

1(2H)-Isoquinolinone (isocarbostyril) (Aldrich) was nitrated using a general method for isoquinoline compounds (C. G. LeFevre and R. J. W. LeFevre, *J. Chem. Soc.* 1470 (1935)). The nitration product (a mixture of the 5-nitro and 7-nitro isomers, as assigned by Y. Kawazoe and Y. Yoshioka, *Chem. Pharm. Bull.* (Tokyo) 16:715–720 (1968), although one of the isomers could be the 8-nitro isomer) was then reduced to the corresponding amino-1(2H)-isoquinolinones using a combination of potassium borohydride and palladium-on-carbon catalyst in aqueous methanol. To the resultant amino-1(2H)-isoquinolinones (as free bases) (0.560 g, 3.50 mmol) in ethyl acetate (175 mL) at 30° C. was added 1.208 g of 3-chloroperoxybenzoic acid (Aldrich). The mixture became cloudy and after 20 minutes it was filtered, extracted with 0.14M sodium bicarbonate (58 mL), washed with two 50-mL portions of water, and dried over sodium sulfate. The volume of the solution was reduced to 50 mL, by rotary evaporation and then placed in the freezer (−20° C.), whereupon an orange solid product was deposited (0.102 g).

Analysis of Reaction Product

Melting point: substance darkens above 175° C., softens, blackens and apparently polymerizes above 195° C., and finally melts in the range 310°–335° C. NMR analysis: $^1$H-NMR (DMSO-d$_6$/D$_2$O, 300 MH$_z$) δ (ppm) from TMS: m (6.723, 6.741, 6.752); m (7.511, 7.518, 7.533, 7.539, 7.547, 7.559, 7.577, 7.585); m (7.663, 7.674, 7.686, 7.698, 7.707); d (7.818, 7.846). In the absence of D$_2$O, the compound also displays a broad singlet at 11.90 ppm. The isomeric components were analytically resolved by thin-layer chromatography (silica gel plates, ethyl acetate solvent), giving two bands, R$_f$ 0.82 and R$_f$ 0.72. Mass spectrum for R$_f$ 0.82: m/z (relative intensity): 174 (M$^+$, 100), 160 (26.8), 144 (93.0), 117 (90.8), 97 (21.9), 89 (96.1), 71 (24.1). High resolution data for the M$^+$ peak: calculated for C$_9$H$_6$N$_2$O$_2$:174.0402928; found: 174.043200 (deviation=−0.3 ppm). For the component having R$_f$ 0.72, M$^+$, calculated for C$_9$H$_6$N$_2$O$_2$:174.042928; Found: 174.043200 (deviation= −1.6 ppm). These data confirm that the compounds are mono-nitroso isomers.

IV. ADPRT Inactivation Studies

The compounds of the subject invention were tested for their ability to inactivate the polymerase activity of adenosinediphosphoribosyl transferase (ADPRT). Assays were performed according to the method of Buki and Kun, *Biochem.* 27:5990–5995 (1988), using calf thymus ADPRT. The assay results as given in Table I provide the I$_{50}$ (the concentration of the compound that inhibits enzyme activity 50%) values for ADPRT of the nitroso precursor (6-amino-1,2-benzopyrone) and the more potent 5-iodo-derivative (Table I, compounds 1 and 2, respectively). The nitroso compounds (3,4,5 in Table I) are all highly active as anti-tumor and anti-HIV molecules (as shown in later sections) and are effective even after exposure of cells for a period as short as 30 minutes. 5-I-6-nitroso1,2-benzopyrone (compound 6) in these studies has been shown to be a relatively poor inhibitor of ADRPT (it is believed that the iodo substitution deactivates the NO group as an electrophile) and its biological action is 10 times weaker than that of 6-N-1,2-benzopyrone. For these reasons, the compositions of the present invention are believed to be superior to 5-I-6-nitroso-1,2 benzopyrone, which has been shown to be a poor permeant molecule.

TABLE I

| No. | I$_{50}$ data for aromatic inhibitors of ADPRT Inhibitor | |
|---|---|---|
| I$_{50}$, μM | | |
| 1 | 6-NH$_2$-1,2-benzopyrone* | 370 |
| 2 | 5-I-6-NH$_2$-1,2-benzopyrone* | 41 |
| 3 | 3-NO-benzamide | 15 |
| 4 | 5(7)-nitroso-(2H)-isoquinolinone** | 13 |
| 5 | 6-NO-1,2-benzopyrone | 40 |
| 6 | 5-I-6-NO-1,2-benzopyrone | 400 |

*biochemical precursor of nitroso compounds 5 and 6
**a mixture of the 5- and 7-nitroso compounds
Assay conditions: ADPRT, 0.4 μg; coDNA, 4 μg; inhibitor diluted between 0.8 and 600 μM, in 50 μl of 50 mM Tris-HCl, 50 mM KCl, 5 mM 2-mercaptoethanol, 0.5 mM EDTA, 0.1 mM NAD ([32-P]-labelled), pH 7.5. Polymerization at 25° C. for 4 minutes.

FIG. 1 illustrates the % inactivation of ADPRT polymerase activity observed after 2 hours of incubation with the nitroso-compound inhibitors at several concentrations.

Additional experiments involving the equilibration between $^{65}Zn^{+2}$ and ADPRT-bound $Zn^{+2}$ suggest that the ADPRT inhibition activity of the nitroso compounds appears to act by destabilizing the protein through the ejecting of $Zn^{+2}$. (Buki K. G., Bauer P. T., Mendeleyev, F. Hakam, H. and Kun E. (1991) *FEBS Lett.* 290:181–185). The above mechanism of action for ADPRT inhibitors is speculative and does not constitute any limitation on claimed subject matter.

V. Biological Anti-Cancer Activities of Nitrosobenzopyrones, Nitrosobenzamides and Nitroso-isoquinolinones Experiments were performed in which various human leukemia cell lines were exposed to increasing concentrations of 6-amino-1,2-benzopyrone (ABP), 5-iodo-6-amino-1,2-benzopyrone (IABP), 6-nitro-1,2-benzopyrone (NO$_2$BP), 6-nitroso-1,2-benzopyrone (NOBP), 3-nitrosobenzamide (NOBA) or 5(7)-nitroso-1(2H)-isoquinolinone (NOQ) (a mixture of the 5-nitroso and 7-nitroso isomers), and the level of [$^3$H] thymidine uptake was determined as a measure of cellular proliferation. As shown in FIG. 2, for each of the cell lines tested (855-2 cells, FIG. 2A; H9 cells, FIG. 2B; HL-60 cells, FIG. 2C; K562 cells, FIG. 2D) the nitroso-containing ligands (NOBP, NOBA, NOQ) were able to inhibit $^3$H-thymidine uptake in lower molar concentrations than the other compounds. NOBP, NOBA and NOQ powerfully inhibited $^3$H-thymidine uptake at a concentration of 10 μM, a concentration at which the other compounds exhibited comparatively slight inhibitory effects.

Experiments with H9 cells grown in 10% fetal bovine serum (FCS) (FIG. 2B) found NOQ to be the most potent inhibitor, demonstrating almost complete inhibition at 10 μM levels. NOBP demonstrated about a 30% decrease in thymidine uptake at 10 μM, and an almost complete inhibition of uptake at 100 μM. NOBA demonstrated about 75% level of inhibition at 10 μM, about 85% inhibition at 100 μM, and almost complete inhibition at 250 μM. The remaining amino and nitro compounds were significantly less potent and did not display complete inhibition until concentrations of 1000 μM were reached.

Experiments with K562 cells grown in 10% fetal bovine serum (FIG. 2D) found NOQ and NOBP to be the most potent inhibitors of cell growth. Both NOQ and NOBP resulted in the almost complete inhibition at concentrations of 10 μM. NOBP was almost as potent as NOQ and produced about 90% inhibition at a concentration of 10 μM, and almost complete inhibition at a concentration of 100 μM. The other 3 compounds tested were significantly less potent.

Experiments with 855-2 cells grown in 10% fetal bovine serum (FIG. 2A) found that NOQ, and NOBP produced almost complete inhibition at a concentration of 10 μM. At a concentration of 1 μM, NOQ produced somewhat more inhibition than NOBP, and NOBP produced somewhat more inhibition than NOBA. Experiments using HL-60 cells (FIG. 2C) provided similar conclusions. The other 3 compounds tested were significantly less potent.

The effect of different growth factors on the growth inhibitory effects of NOBP was tested. 855-2 cells that were grown in media with (1) 10% fetal bovine serum, (2) autocrine growth factor (AGF) and (3) low molecular weight-BCGF (a T cell derived lymphokine) were exposed to increasing concentrations of the ADRPT ligands. The results are provided in FIG. 2(A, E, F). Cells grown in each of the growth factors were all potently inhibited by the nitroso-containing compounds, with concentrations of 5 to 10 μM resulting in 100% inhibition, Thus, NOBP, NOBA and NOQ exert potent inhibitory effects regardless of the source of growth factor activity.

Figure 3:
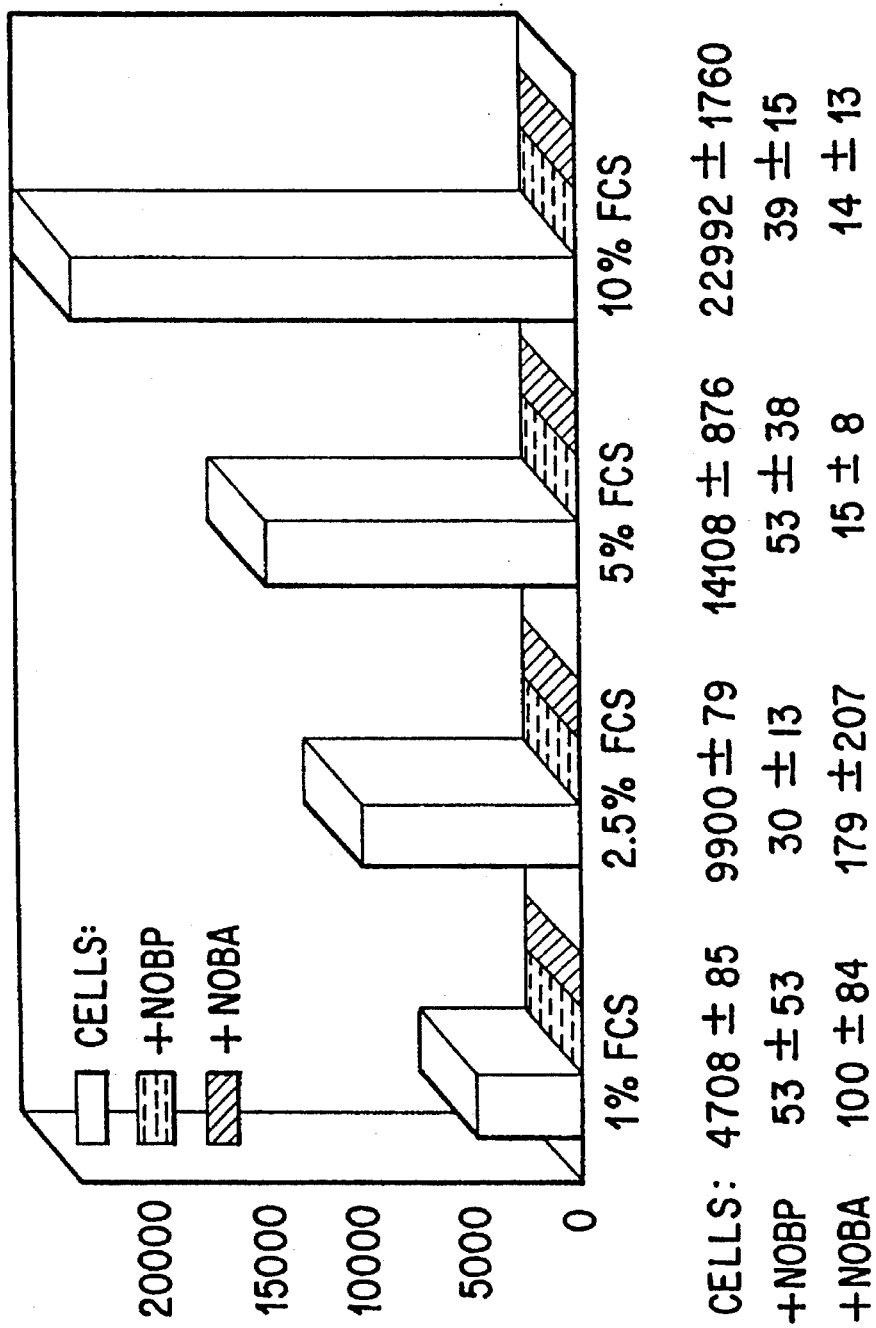
FIG. 3 is a graph showing the inhibition of increasing levels of leukemic cell growth (in response to increasing concentrations of FCS) of 855-2 cells by 6-nitroso-1,2-benzopyrone (NOBP) and 3-nitrosobenzamide (NOBA).
Figure 4:
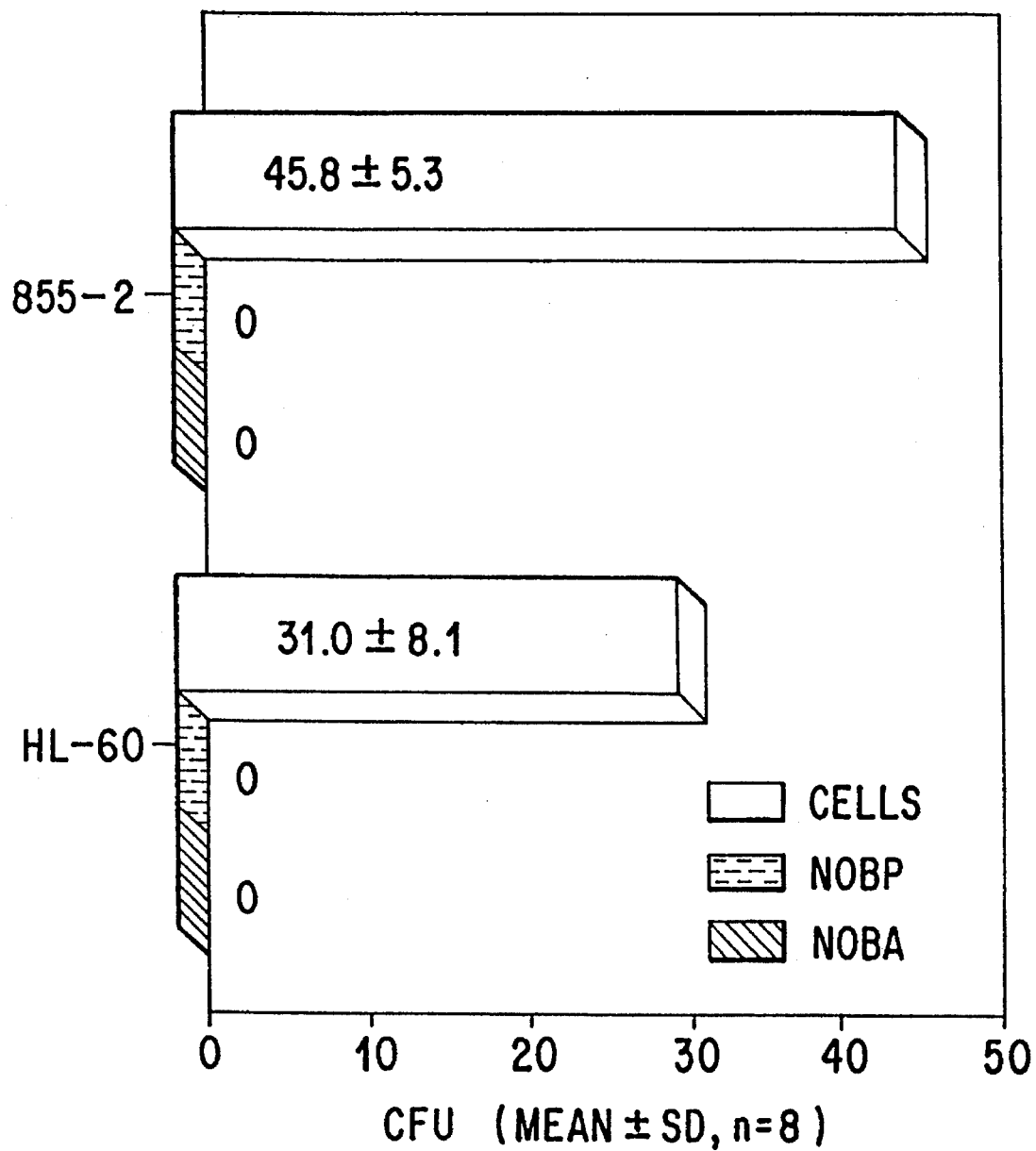
FIG. 4 is a graph showing that NOBP and NOBA inhibit the ability of human leukemic cells (855-2 and HL-60) to form colonies (CFU) from single cells in a semi-solid medium.
Figure 5A:
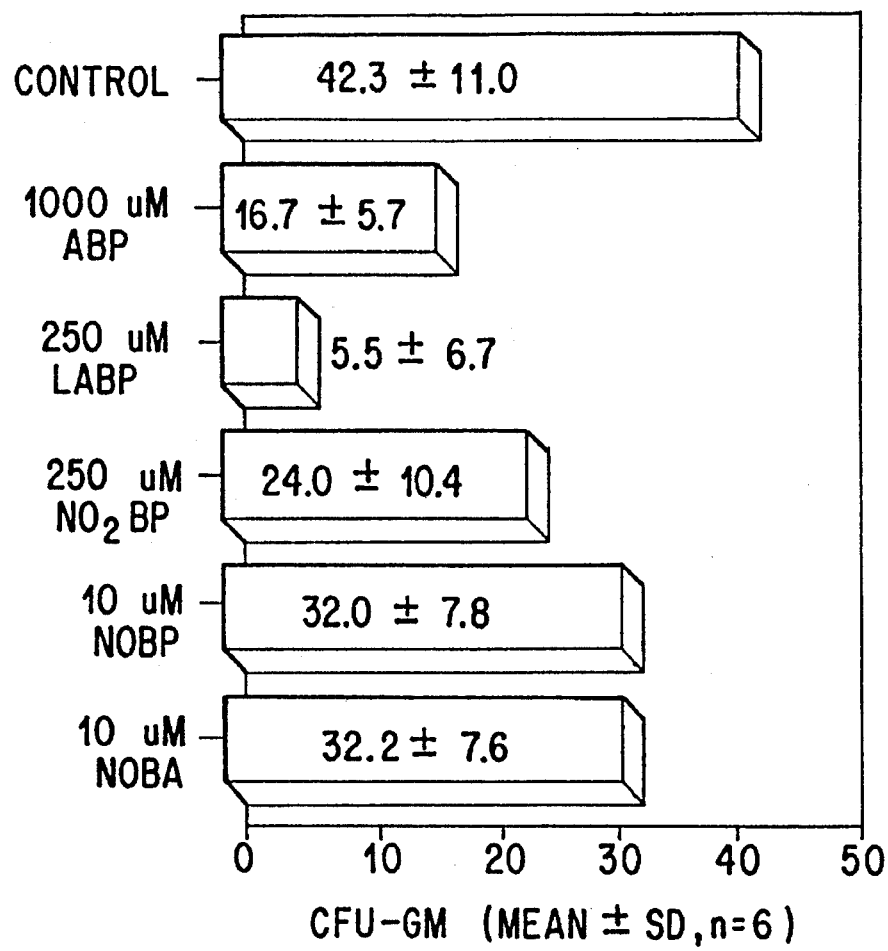
FIGS. 5a–5B show graphs of the relative inhibitory effects of anti-leukemic doses of ADRPT ligands on the ability of (FIG. 5A) normal rhesus bone marrow stem cells or (FIG. 5B) human peripheral blood stem cells to form colonies in soft agar. Note that the NOBP and NOBA had minimal effect on normal cells.
Figure 5B:
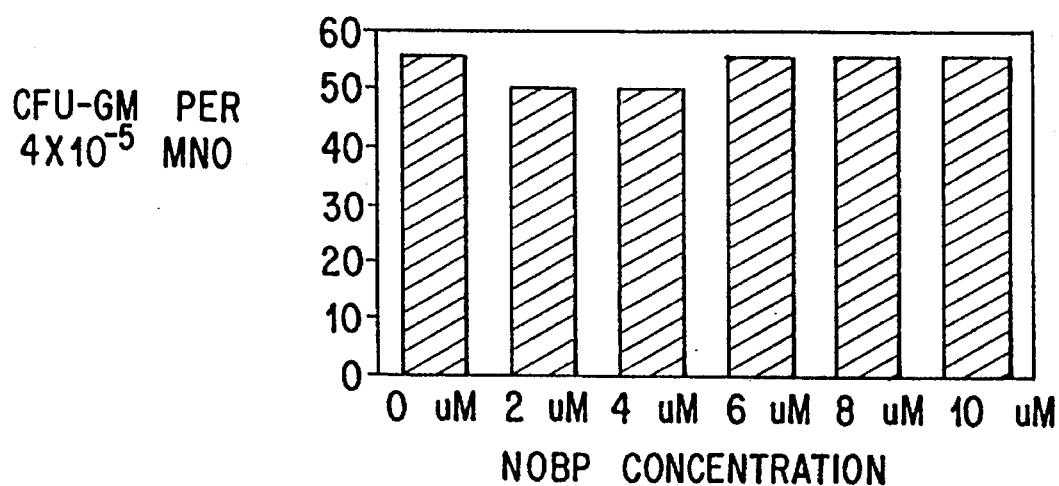
Figure 6A:
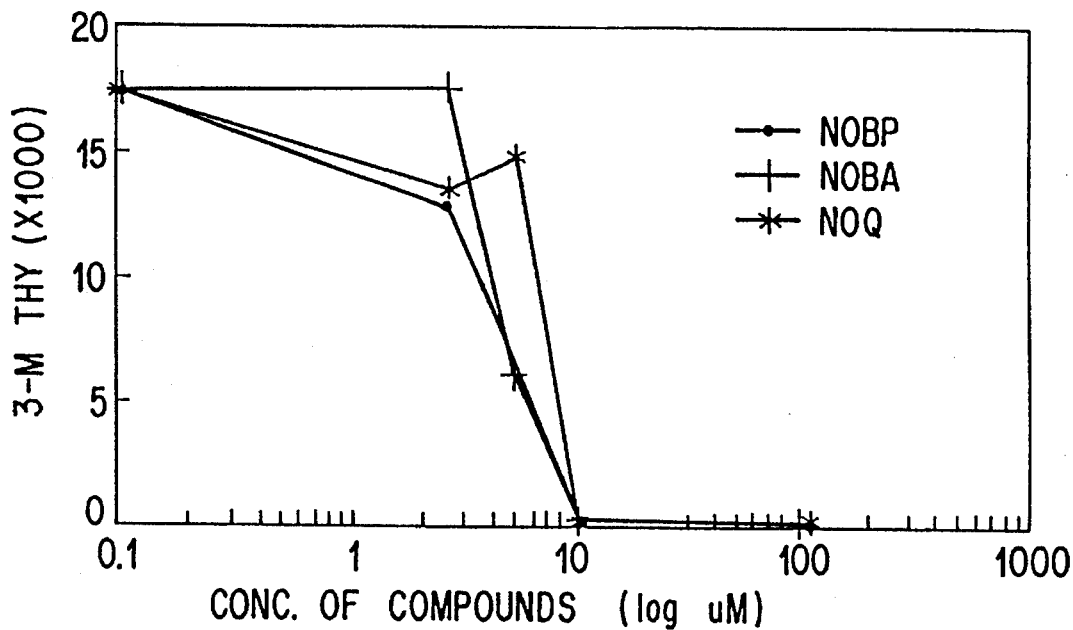
FIGS. 6A–6D show displaying the inhibitory effects of NOBP, NOBA and NOQ on four human brain tumor cell lines.
Figure 6B:
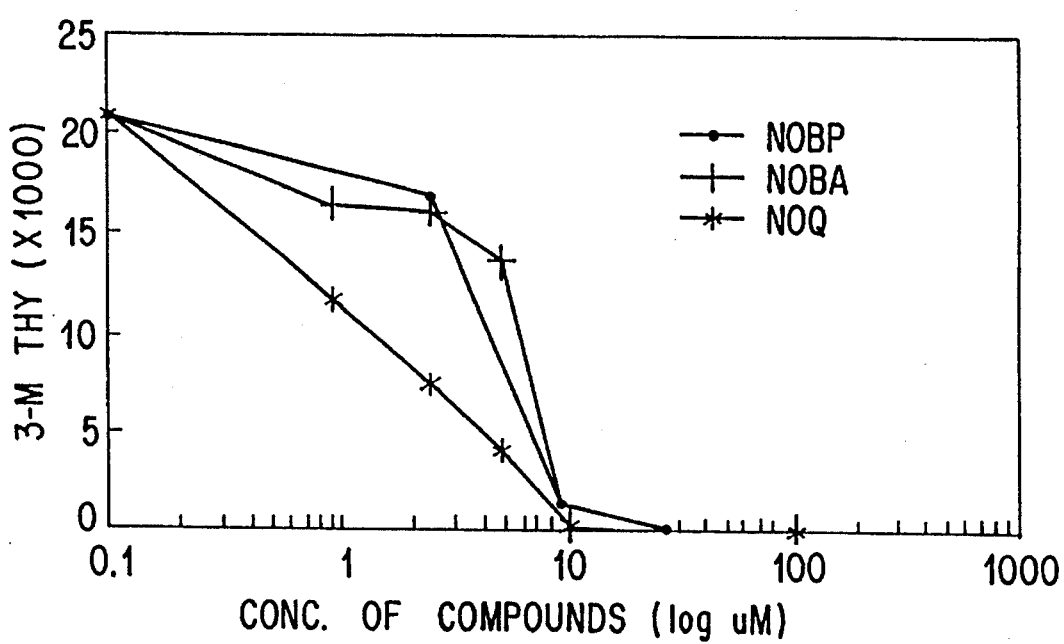
Figure 6C:
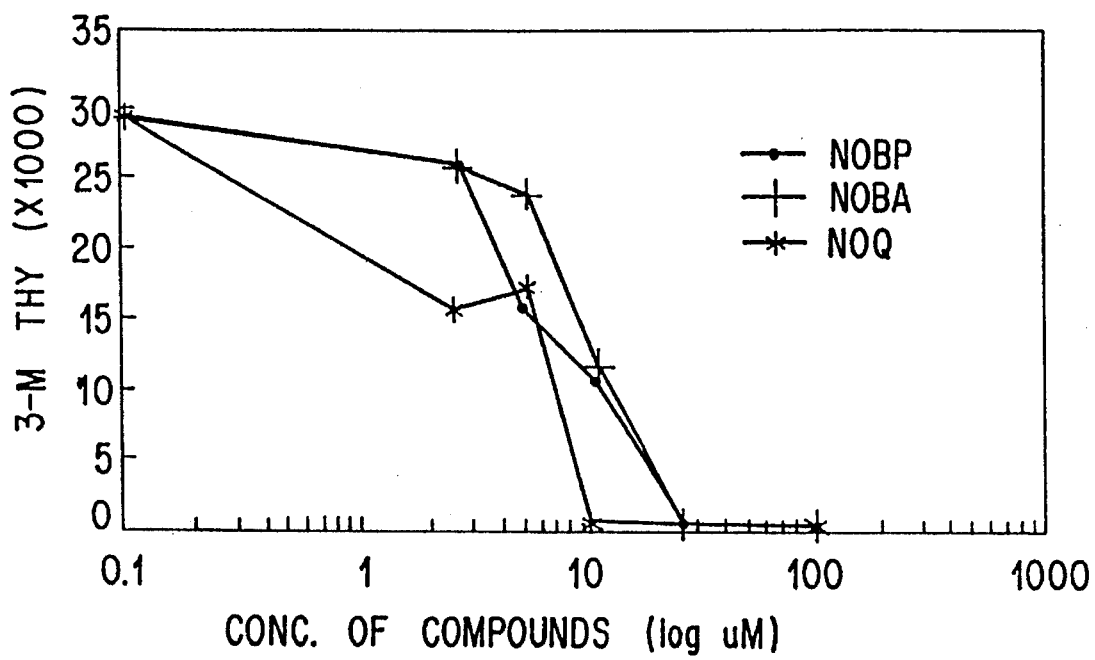
Figure 6D:
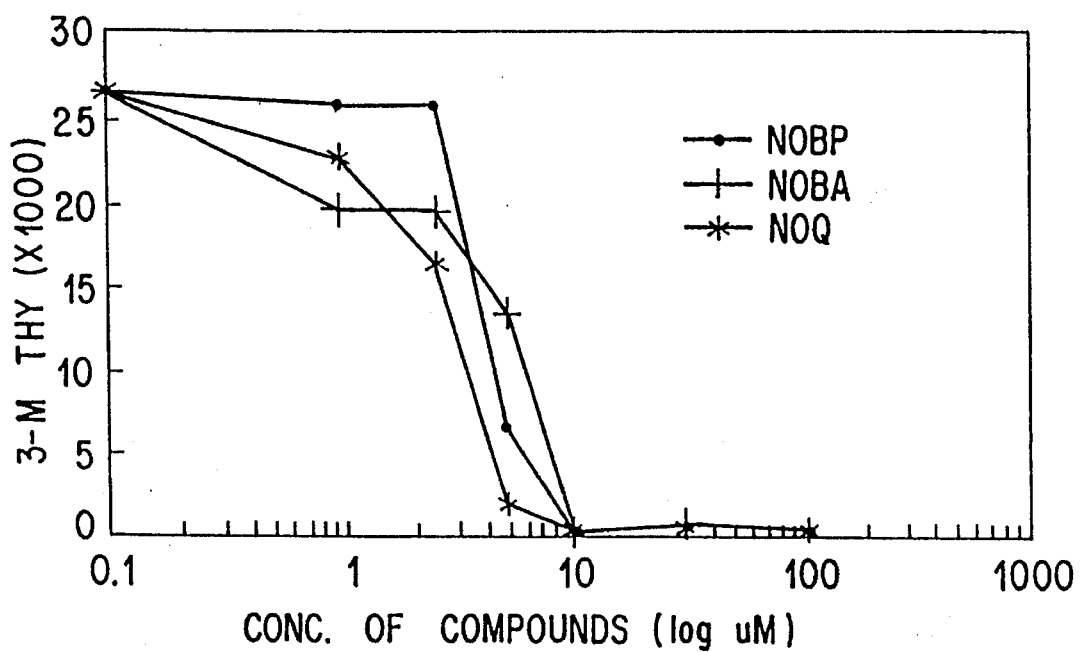

In order to exclude the possibility that NOBP and NOBA manifest their growth inhibitory effects through inactivation of growth factors, the effects of 10 μNOBP or NOBA (constant concentration) on 855-2 cells in the presence of increasing concentrations of fetal bovine serum (FCS) were tested (FCS) contains growth factors for 855-2 cells). The data are provided in FIG. 3. Growth arrest occurs irrespective of the concentration of FCS. Thus, the mode of action of NOBP, does not appear to be by antagonism of growth factors but at ADPRT sites related to DNA-replication.

In preliminary experiments the propagation of L1210 murine leukemia was also tested in vivo and the results showed that NOBA injected intraperitoneally at a dose of 2 mg/kg twice a day for 6 consecutive days, causing no toxic effects, prolonged the life of BDF mice from 10 days (untreated) to 35 days (end of observation), thus exerting a highly significant in vivo chemotherapeutic response. These results are somewhat suprising in light of the high levels of ascobic acid present in mice. Ascorbic acid, a strong reducing agent, reduces 3-NOBA. In its reduced form 3-NOBA is not as effective at removing zinc from zinc fingers. Hence, one would not expect 3-NOBA to be as an effective chemotherapeutic agent in the presence of high levels of ascobic acid.

Tumor cell inhibitory concentrations of NOBP and NOBA were shown not to affect adversely the viability of normal cells. Experiments were performed in which the functions of various cancer cells (855-2 and HL-60 leukemia cells, D32, D37 and CRL 7712 glioblastoma cell lines, 186 medulla tumor cell line, L1210 murine leukemia cell line, MDA-468 human breast tumor cell line) and normal cells (neutrophil leukocytes and bone marrow or peripheral blood stream cells) were assessed in the absence or presence of the compounds. The results are shown in FIGS. 4–9. Together, the data indicate that a concentration of 10 μM of the nitroso-containing ligands effectively suppressed cancer cell growth but demonstrated only modest effects the functions on normal cells.

VI. Toxicity of NOBP

The cytotoxicity of 0, 2 μM, 4 μM, 8 μM and 10 μM NOBP was measured by examining the effect of the compound on the colony formation (CFU-GM) of normal human stem cells (PBSC). The results of the experiments are provided in FIG. 5B. Toxicity was not detected, even though levels of NOBP sufficient to block 855-2 cell proliferation completely were tested.

A similar CFU stem cell toxicity assay was performed in which comparisons were made between (ABP) 6-amino-1,2-benzopyrone 1 μM (IABP) 5-I-6-amino-1,2-benzopyrone 250 μM, (NO$_2$BP) 6-nitro-1,2-benzopyrone (weakly active) 250 μM, NOBP 10 μM, and NOBA 10 μM. The results of the experiments are provided in FIG. 5A. Whereas the 6-amino-1,2-benzopyrone, 5-I-6-amino-1,2-benzopyrone and the 6-nitro derivative were toxic at the tested given doses, the almost ineffective (against tumor cells) 6-nitro derivative and the highly effective (against tumor cells) NOBP and NOBA were non-toxic.

The effects of 10μm NOBP and NOBA on superoxide generation by normal human peripheral blood neutrophil leukocytes was tested. The results are provided in Table II. Only minor reductions in superoxide generation were observed.

TABLE II

Effects of 10 μM NOBP and NOBA on the
Generation of Superoxide by Human Neutrophils

| cells | nmol $O_2^-$/hr/$10^5$ (mean + S.D., n = 11) |
|---|---|
| $10^5$ PMN + PMA: | 55.9 ± 7.7 |
| +10 μM NOBP | 34.1 ± 14.1 |
| +10 μM NOBA | 44.4 ± 10.0 |

VII. Comparative Efficacy Studies

Figure 7:
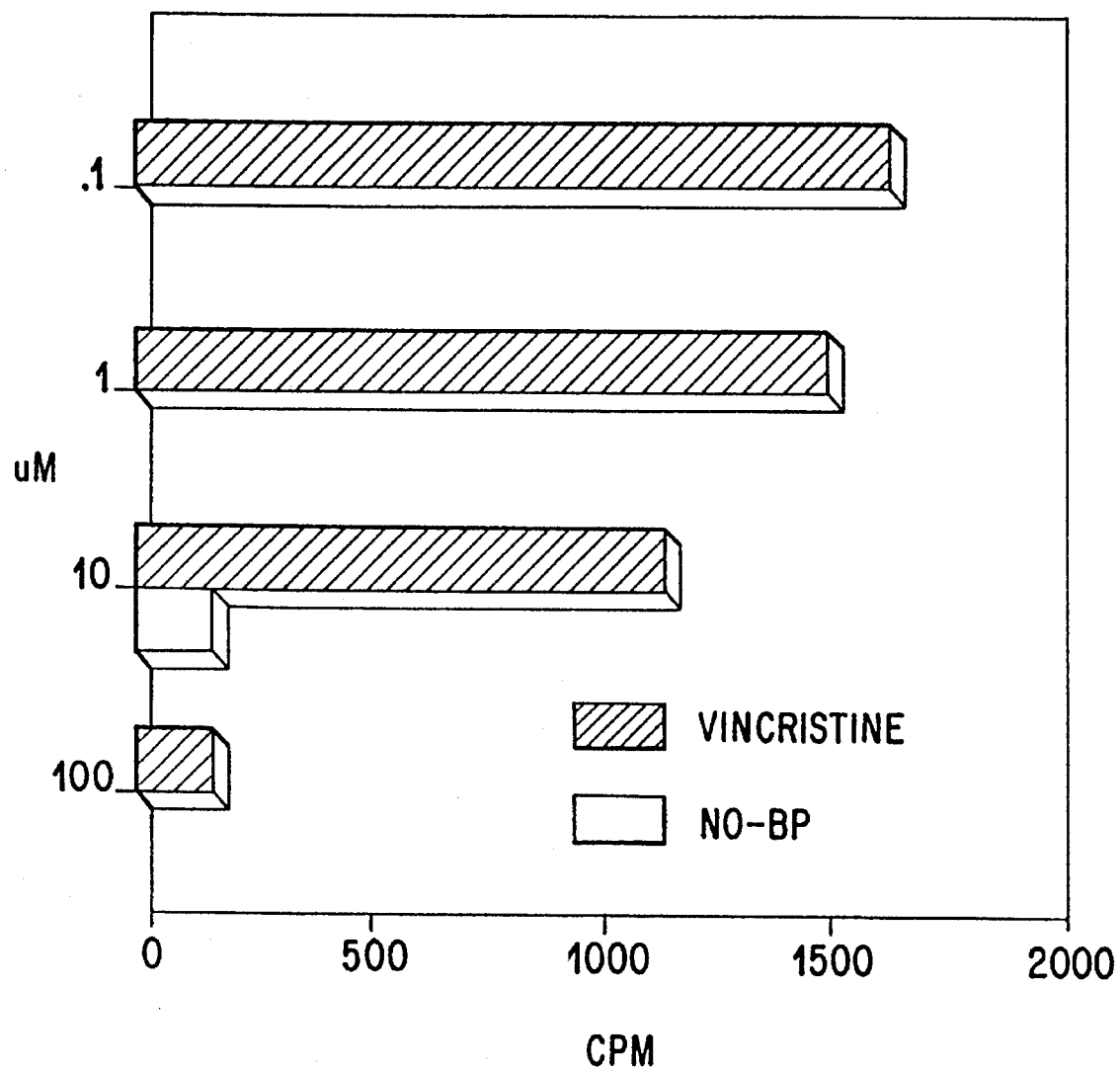
FIG. 7 is a graph comparing the effectiveness of NOBP with vincristine.
Figure 8:
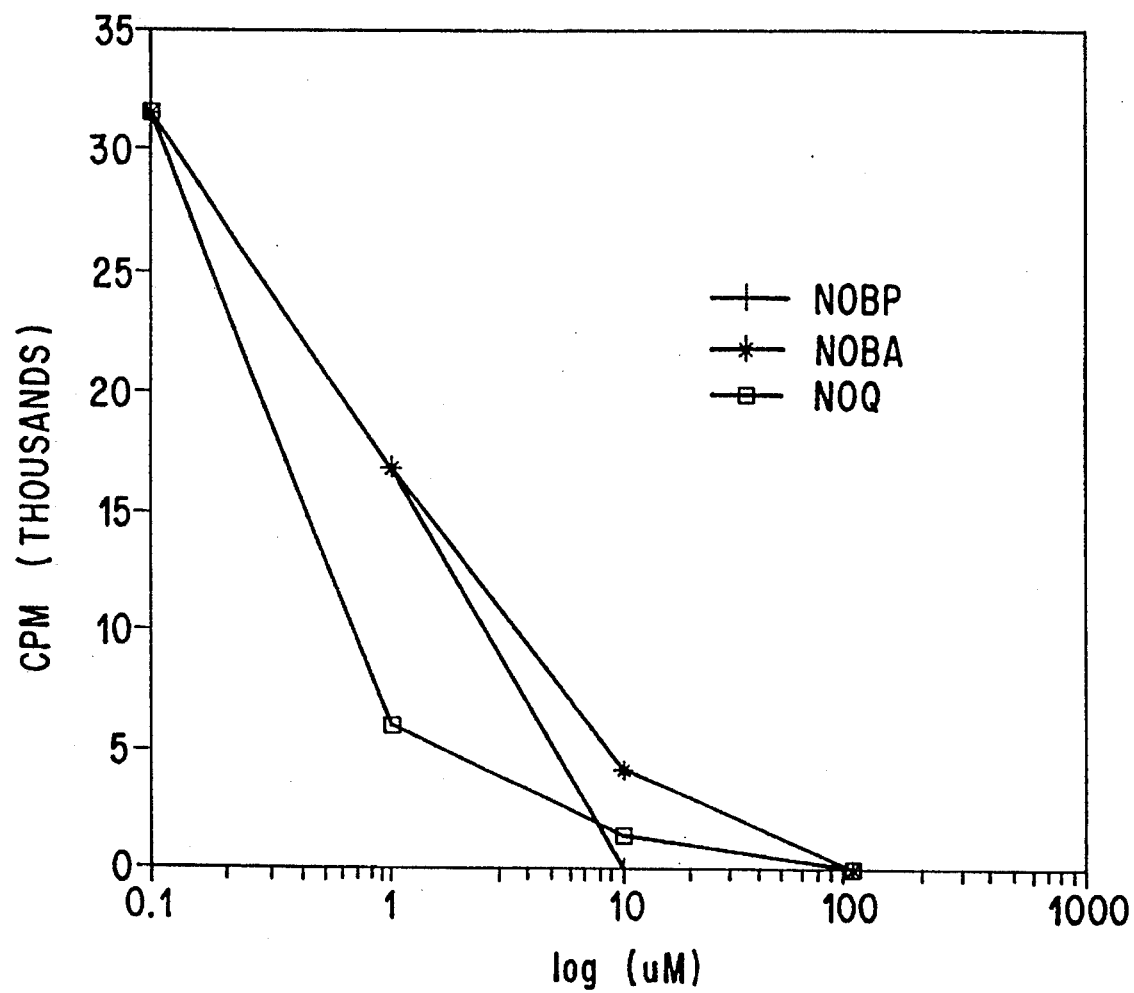
FIG. 8 is a graph displaying the effects of NOBP, NOBA and NOQ on human breast tumor cell line MDA 468.
Figure 9:
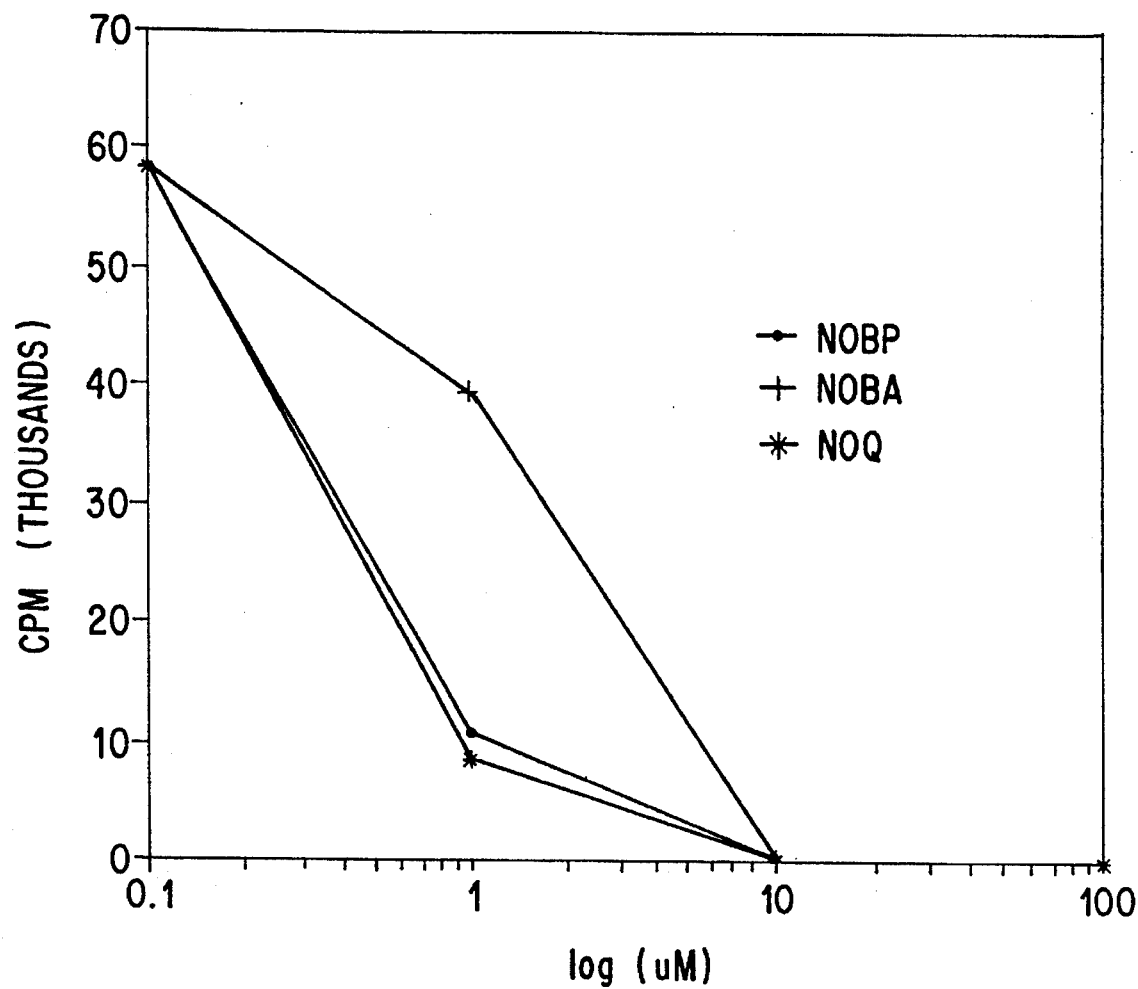
FIG. 9 is a graph displaying the effects of NOBP, NOBA and NOQ on murine leukemia cell line L 1210.

Vincristine, a highly toxic chemotherapeutic compound, is currently used in the treatment of leukemia and other malignancies. Studies were performed in order to determine the concentration of vincristine that produces the same level of growth inhibition as 10 μM NOBP, when assayed on 855-2 leukemia cells grown in vitro. Vincristine was tested in doses of 0.1, 1, 10 and 100 μM. As shown in FIG. 7. 100 μM of vincristine (a highly toxic concentration) was required to produce the same level of inhibition as 10 μM of NOBP, thus NOBP is about 10 times more potent than an equal concentration of vincristine, and is not toxic to normal cells.

Thus certain aromatic nitroso molecules that are also inhibitors of ADPRT polymerase activity may be useful chemotherapeutic cytostatic agents because of their effectiveness combined with low toxicity..

VIII. Anti-HIV action of NOBP, NOBA and NOQ on stimulated human lymphoblasts.

The ability of NOBP (6-nitroso-1,2-benzopyrone) and NOBA (3-nitrosobenzamide) to inhibit HIV infections were tested using the methods described in the *Journal of Immunological Methods* 76:171–183 (1985). Exposure to the two drugs was only for 30 minutes at the commencement of viral infection, and drugs were never re-added. The results given in Table III provide the $ID_{50}$ of HIV titer 10 days after infection of cell cultures with HIV. The data in Table III demonstrate that, 10 μM of the nitroso-containing ligands causes a three log decrease in the HIV-1 infectivity titer.

TABLE III

| Test Sample days | Virus Titer (log $ID_{50}$) 10 |
|---|---|
| Virus Alone | 5.25 |
| +500 μM ABP | 4.50 |
| +250 μM IABP | 4.66 |
| +250 μM $NO_2BP$ | 4.93 |
| +10 μM NOBP | 2.01 |
| +10 μM NOBA | 1.05 |
| +10 μM NOQ | 1.73 |

IX. Cytocidal Activity of ADRPT ligands—MTT Assay

Experiments were performed to determine if the inhibition of proliferation of 855-2 cells seen in culture and in soft agar is due to the cytostatic or cytocidal effect of the nitroso compounds NOBP, NOBA, and NOQ. Cells at 1×$10^5$/ml (concentration used in bone marrow assay) were treated with NOBP, NOBA and NOQ at 1, 2.5, 5 and 10μm for 2 hours then stimulated with 10% fetal calf serum and incubated for 24 hours. MTT (3-[4,5-Dimethyl-2-yl]-2,5-diphenyltetrazolium bromide) at 1 mg/ml was then added for 16 hours. The absorbance of the pelleted cell was then measured at 550 nm after adding DMSO to solubilze the cells.

Results: With 10 μM NOBP, NOBA and NOQ, complete killing was observed in 855-2 cells at 100,000/ml.

X. NMR STUDIES OF $Zn^{+2}$ EJECTION FROM Zn (HIV1-F1)

Figure 10:
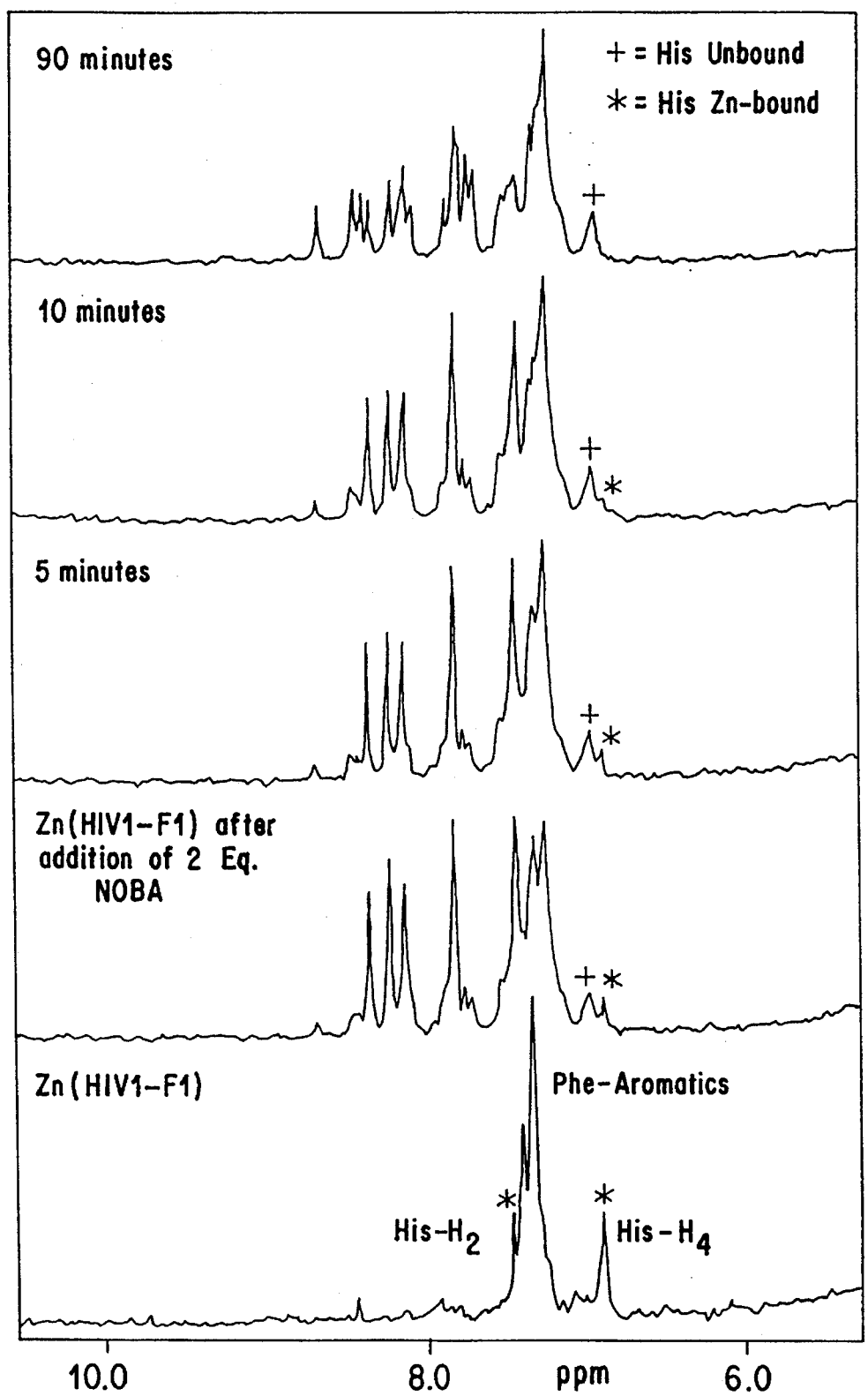
FIG. 10 shows the downfield region of the $^1$H NMR spectrum obtained for Zn(HIV1-F1)(1 mM in D$_2$O solution, pH*=6.2, T=30° C.)(bottom) and upon addition of NOBA (2 mM). The * and + symbols denote the aromatic proton signals of the zinc-coordinated and zinc-free His 9 residue. Upon completion of the reaction, reflected by complete ejection of zinc (t=90 min), 50% of the NOBA remained unreacted indicating a 1:1 reaction stoichiometry. NOBA (3-nitrosobenzamide), was synthesized described elsewhere in this application.

To determine if NOBA is capable of ejecting zinc from retroviral-type zinc fingers, NMR studies were performed on a peptide with amino acid sequence corresponding to the N-terminal CCHC zinc finger of the HIV-1 NC protein, Zn(HIV1-F1), South, et al., *J. Am. Chem. Soc.* 111:395–396 (1989), South, et al., *Biochem Pharm.* 40:123–129 (1990), Summers, et al., Biochemistry 29:329–340 (1990). NMR spectra of Zn(HIV-F1) were performed before and after the addition of NOBA (3-nitrosobenzamide). Previous NMR studies have demonstrated that this peptide binds zinc stoichiometrically and with high affinity, South, et al., *J. Am. Chem Soc.* 111:395–396 (1989), and three-dimensional structural studies have shown that the peptide adopts a structure that is essentially identical to the structure of the corresponding region in the intact NC protein, South, et al., *Biochemistry* 29:7786–7789 (1990). NMR spectra of Zn(HIV-F1) were performed before and after the addition of NOBA (3-nitrosobenzamide). The down-field region of the $^1H$ NMR spectrum showing the signals due to the aromatic proton of His 9 and Phe 2 is illustrated in FIG. 10 (bottom). Addition of two molar equivalents of NOBA results in the loss of the signals due to zinc-bound histidine (denoted by *) and the appearance of broad signals representative of zinc-free histidine (denoted by +). Other signals in the spectrum are due to NOBA protons. After 90 min., no signals attributable to the zinc-bound His could be detected, see FIG. 10. After 90 minutes, the signals due to unreacted NOBA were of equal intensity compared to the reacted NOBA signals, indicating that NOBA reacts stoichiometrically with Zn(HIV1-F1); this finding has been confirmed by additional studies with one equivalent of NOBA. By comparison, a 10-fold molar excess of EDTA is required to remove zinc from Zn(HIV-1-F1), Summers, et al., *J. Cell Biochem* 45:41–48 (1991).

XI. NMR STUDIES OF Zn(HIV1-F1) NUCLEIC ACID BINDING

Figure 11:
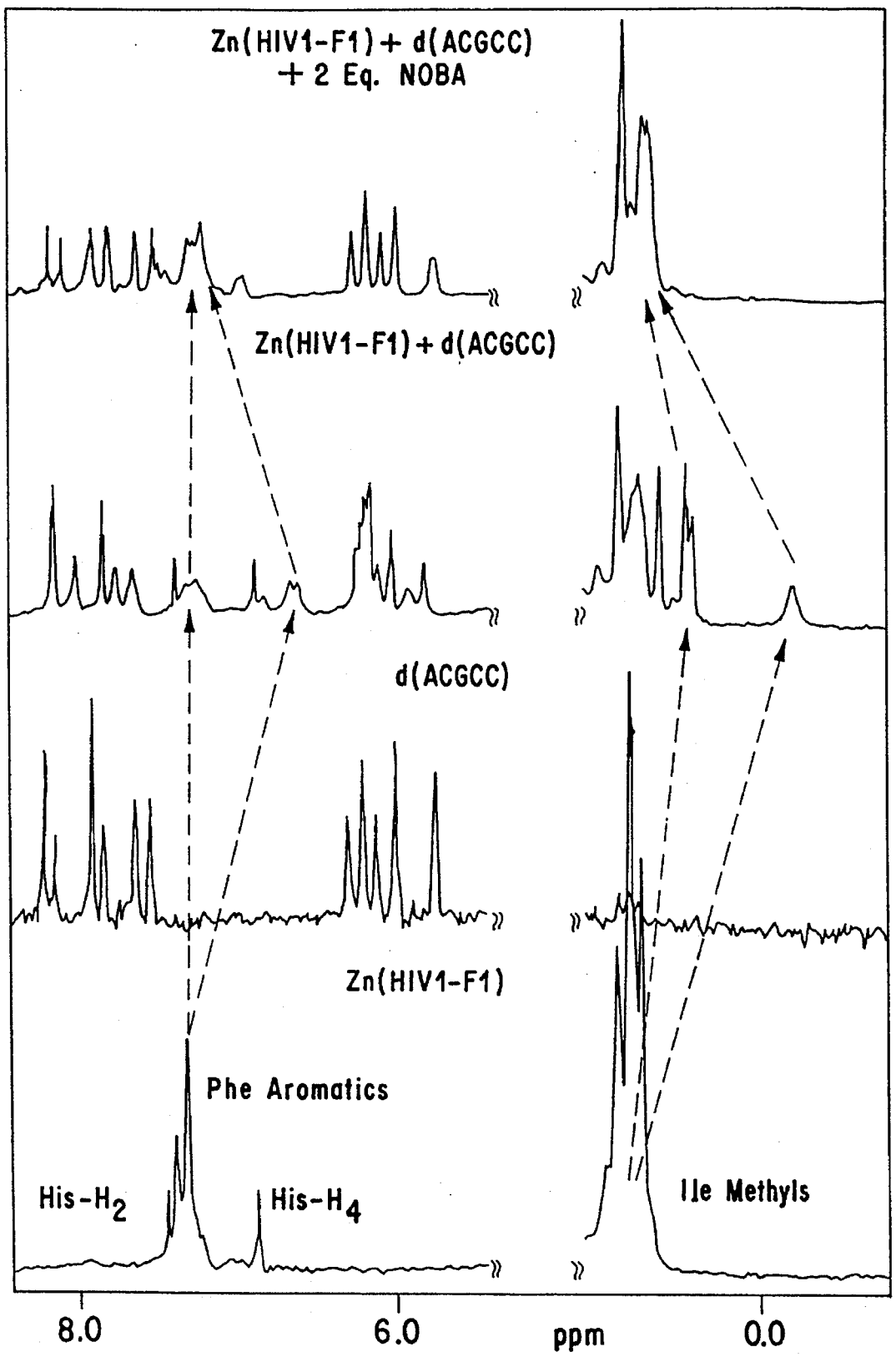
FIG. 11 shows selected regions of the $^1$H NMR spectrum obtained for Zn(HIV1-F1)(bottom) and a synthetic oligonucleotide with sequence corresponding to a region of the HIV-1 Psi-packaging signal, d(ACGCC)(2nd from bottom). The downfield regions of the spectra show the signals of the aromatic and ribose H1' protons, and the upfield region contain signals of the methyl group protons. Dramatic spectral changes occur upon addition of oligonucleotide to Zn(HIV1-F1), including large upfield shifts of the Phe 2 and Ile 10 side chain=n signals and a downfield shifting and broadening of the guanosine-H8 proton signal (second from the top). After incubation with two equivalents of NOBA, the spectral features are characteristic of metal-free peptide and dissociated nucleic acid (top), indicating that NOBA-induced zinc ejection leads to loss of high-affinity nucleic acid binding function.
Figure 12:
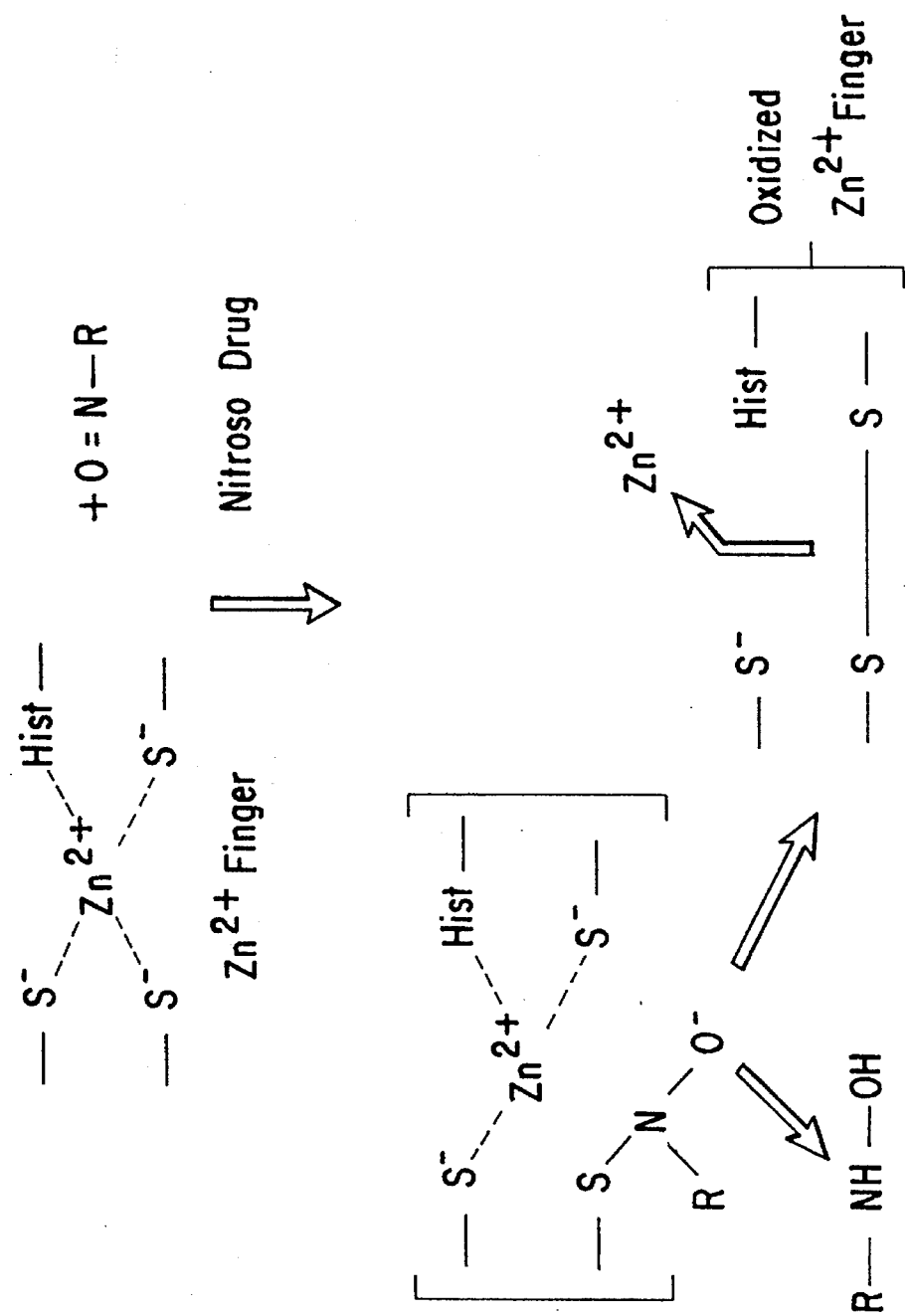
FIG. 12 shows the proposed mechanism for the ejection of Zn$^{+2}$ from Zn(HIV1-F1) by NOBA (3-nitrosobenzamide).

Zn(HIV1-F1) has been shown to bind to single-stranded nucleic acids with sequence specificity, and a highly stable complex with a 5-residue oligonucleotide, d(CACGCC), containing the sequence of a portion of the HIV-1 Psi-packaging signal has been prepared for high-resolution structural studies. Experiments have been performed indicating that the addition of NOBA to this protein-oligonucleotide complex results in ejection of zinc with concomitant dissociation of the zinc finger nucleic acid complex, (FIG. 11). These data indicate that the CCHC array ($Cys-X_2-Cys-X_4-His-X_4-Cys$) of the HIV-1 NC protein Zn(HIV1-F1) can be specifically affected by NOBA so that functional binding to nucleic acid substrates is abated. The reaction mechanism, schematically illustrated in FIG. 12, is consistent with the result of NMR analysis in FIGS. 10 and 11. The reaction mechanism proposed in FIG. 12 is a useful model but is not intended to limit the scope of the claimed invention.

XII. ZINC LOSS RESULTING FROM TREATMENT OF HIV-1 VIRIONS WITH NOBA

Experiments were performed to determine if NOBA is capable of ejecting zinc from intact virions. HIV-1(MN strain) was produced, purified and concentrated as described in Bess et al., *J. Virol.* 66:840–847 (1992). The concentrated virus was diluted to 60 times that of culture fluid in TNE buffer (0.01 M Tris-HCl, 0.1M NaCl, 1 mM EDTA, pH 7.2) and incubated with 3000 or 6000 μM NOBA at 37° C. The virus was then pelleted and washed with TNE buffer to remove weakly bound zinc. The quantity of zinc in the resulting viral pellets was determined as described in Bess et al., *J. Virol.* 66:840–847 (1992). No significant loss of viral proteins in the pellet was detected by p24 and gp120 competition radioimmunoassays and comassie-stained sodium dodecyl sulfate polyacrylamide gel electrophoresis.

The data in Table IV demonstrate that treatment of concentrated suspensions of HIV-1 (60x with respect to culture solution) with NOBA results in losses of 50–83% of the viral zinc and complete loss of infectivity. Since edge x-ray absorption fine structure spectroscopy has shown that the majority of the zinc in intact retroviruses is coordinated by the CCHC ligands (Summers, et al., *Protein Science* 1:563–574 (1992) and Chance et al., *Proc. Natl, Acad. Sci.* 89:(1992) in press)), the ejection of zinc from virions by NOBA is directly attributable to a destabilization of the nucleocapsid CCHC zinc fingers. Anti-HIV activity for R-$NH_2$ type ligands of poly(ADP-ribose) polymerase (Cole et al., *Biochem. Biophys. Res. Commun.* 180:504–514 (1991)) may now be attributed, in part, to destabilization of retroviral CCHC zinc fingers since R-$NH_2$ compounds are metabolic precursors of R-NO type molecules (Buki, et al., *FEBS Lett.*, 290:181–185 (1991)).

TABLE IV

| NOBA ($\mu M$)[b] | Incubation time (h) | Zinc, Control Sample ($\mu g/ml$) | Zinc, NOBA-Treated Sample ($\mu g/ml$) | Zinc Loss (%) |
|---|---|---|---|---|
| 3,000 | 2 | 0.21 | 0.11 | 52 |
| 6,000 | 4 | 0.24 | 0.04 | 83 |

[b]Concentrations correspond to molar NOBA:zinc finger ratios of ca. 350:1 (3,000 $\mu M$) and 700:1 (6,000 $\mu M$)

XIII. IN VIVO TESTING OF NOBP AND NOBA

Figure 13A:
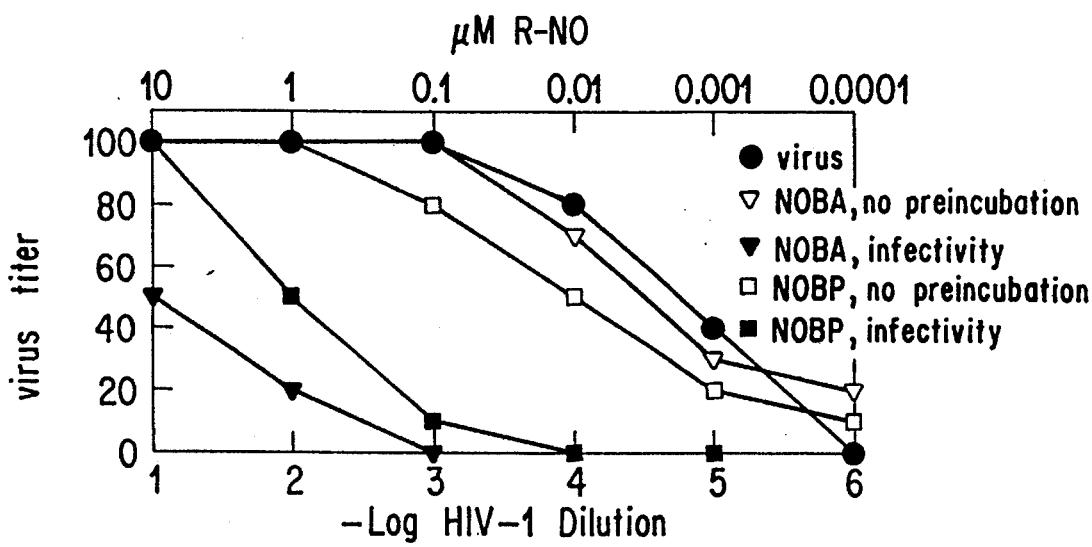
FIG. 13 A. shows the HIV-1 inactivation assay using NOBA and NOBP (6-nitroso-1,2-benzopyrone). The HIV-1 stock (HIV-1 100,000 TCIDs$_{50}$ was treated for 30 Min. with 100 μM NOBA or 100 μM NOBP at 22° C., the mixture was serial 10-fold diluted and inoculated into PBL cultures. After 9 days the culture supernatants were harvested and the frequency of infected cultures was measured by immunoassay. The percent positive of cultures was then plotted as a function of the virus input titer. The relative amount of infectious virus available to cause 50% infected cultures was decreased by 4 log units with NOBA. NOBP was synthesized by the methods described below.
Figure 13B:
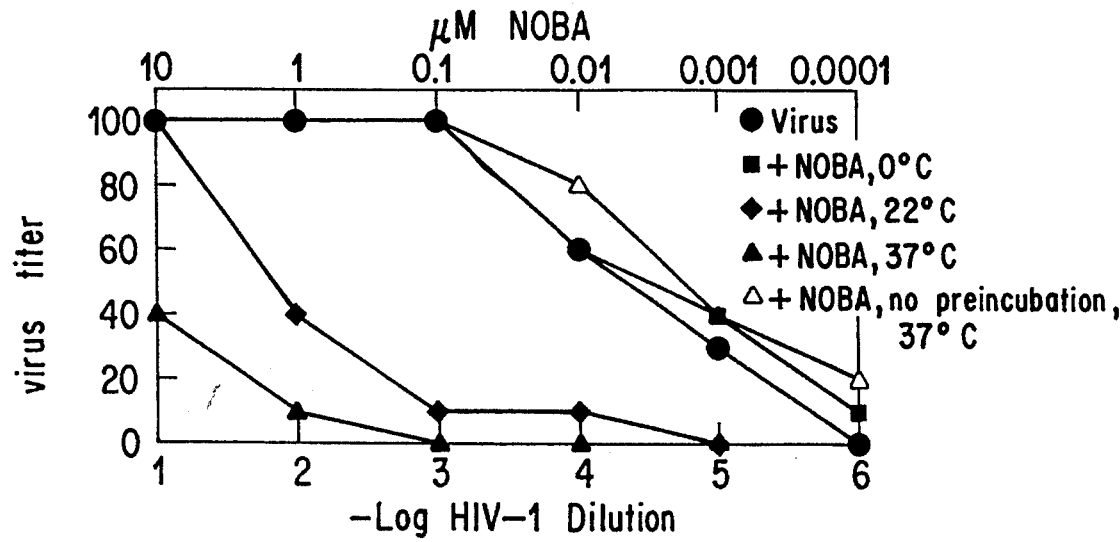
Figure 13C:
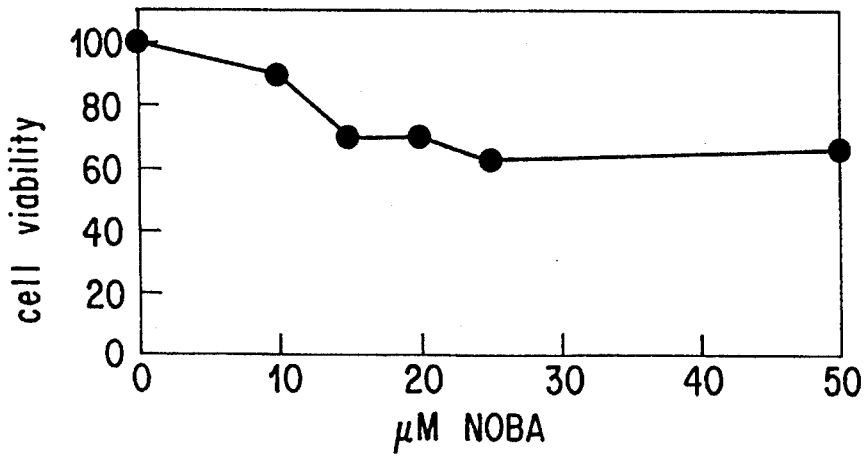

Both NOBP (6-nitroso-1, 2-benzopyrone) and NOBA were tested on viral growth of HIV-1 (LAV strain) in phytohemagglutinin-stimulated human peripheral lymphocytes (PBL) as follows. An HIV-1 stock having an infectivity titer of 100,000 $TCID_{50}$ was incubated for 30 min. at 22° C. with either of the drugs. Control HIV samples, containing no drugs, were incubated in the same manner. Following successive serial dilutions of 10-fold that resulted in HIV-1 titers as giver in the lower abscissa of FIG. 13 (A,B), viral growth was initiated by adding the HIV-1 dilutions to PBL and allowing an incubation period of 9 days. At the end of this incubation cultures were assayed for productive infection by an immunoassay for HIV-1 antigens and by reverse transcriptase as described in McDougal, et al., *J. Immunol Methods* 76:171–183 (1985). Virus titers were expressed as percentile values (percent infected cultures) compared to the controls, containing HIV dilutions which were not preincubated with the C-nitroso drugs. In a separate series of experiments, HIV-1 dilutions and C-nitroso drugs (see upper abscissa) were not preincubated but were added simultaneously to lymphocytes in exactly the same concentrations as described previously (i.e., following preincubation) and viral growth monitored 9 days later. As illustrated in FIG. 13, South, et al., *J. Am. Chem. Soc.* 111:395–396 (1989), South, et al., *Biochem Pharm.* 40:123–129 (1990), Summers, et al., *Biochemistry* 29:329–340 (1990), the inhibition of HIV-1 propagation was profound when C-nitroso drugs were preincubated with HIV-1, whereas only negligible effect on HIV-1 growth occurred when both drugs and virus were added simultaneously. Between the two C-nitroso drugs, NOBA induced a greater depression of HIV-1 propagation.

Experiments were performed in which the incubations with NOBA was carried out at 0°, 22°, and 37° C. From FIG. 13B it is apparent that inactivation of HIV-1 by NOBA occurred maximally at 37° C., suggesting a probable lesser accessibility of the viral zinc finger to the drugs as compared to the Zn(HIV-1-F1) present in the isolated polypeptide (FIGS. 10 and 11). In agreement with the negligible cytotoxic effect of C-nitroso drugs on nontumor cells described elsewhere in this application, human lymphocytes tolerated NOBA up to 50 $\mu M$ without major changes in cell metabolism, which was assayed by quantitative dye reduction as described in Mosaran, *J. Imm. Methods* 65:55–63 (1983).

The direct action of C-nitroso drugs on a critical molecular structure of the HIV-1 virus itself, the zinc finger of NC protein, distinguishes these drugs from any presently known chemotherapeutic agents. Metabolic precursors of C-nitroso drugs, which are R-$NH_2$ type ligands of poly (ADP-ribose) polymerase, suppress HIV-1 replication of both MT-2 an Aa-2 cells, Cole, et al., *Biochem. Biophs. Res. Comm.* 10:504–514 (1991). Correlation between the inhibitory binding of these R-$NH_2$ ligands to poly (ADP-ribose) polymerase and their anti-HIV effectively indicates the participation of this nuclear enzyme in the mode of action of these molecules as antiviral agents. However the concentration of the R-$NH_2$ drugs required to block HIV-1 replication is about $10^3$ higher than the effective antiviral concentration of C-nitroso drugs. Considering the relatively slow rate of the oxidation of R-$NH_2$ drugs to C-nitroso molecules (Buki, et al., *FEBS Letters* 290:181–185 (1991)) in cells, the relatively high concentrations (millimolar) of R-$NH_2$ drugs correspond to their role as "pre-drugs" or sources of C-nitroso type molecules which are effective in micromolar concentrations. Therefore a direct action of C-nitroso drugs formed from their precursors is feasible, although it cannot be ruled out at present that these drugs, besides acting directly on HIV-1 as shown here—may have an additional mode of action that could be related to the effects of C-nitroso drugs as apoptosis-inducing agents in cancer cells.

All publications, patents, and patent applications cited above are herein incorporated by reference.

The-foregoing written specification is considered to be sufficient to enable one skilled in the art to practice the invention. Indeed, various modifications of the above-described modes for carrying out the invention which are obvious to those skilled in the field of pharmaceutical formulation or related fields are intended to be within the scope of the following claims.

What is claimed is:

1. A compound having the formula:

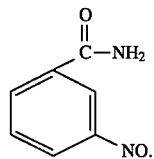

2. A pharmaceutical composition, said composition comprising a pharmaceutically effective amount of
   (a) 3-nitrosobenzamide; and
   (b) a pharmaceutically acceptable amount of an inert carrier.

* * * * *